United States Patent
Drake et al.

(10) Patent No.: US 11,931,523 B2
(45) Date of Patent: Mar. 19, 2024

(54) LEAD DELIVERY DEVICE AND METHOD

(71) Applicant: Medtronic, Inc., Minneapolis, MN (US)

(72) Inventors: Ronald A. Drake, St. Louis Park, MN (US); Stanten C. Spear, Arden Hills, MN (US); Lindsey M. Tobin, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 723 days.

(21) Appl. No.: 16/983,597

(22) Filed: Aug. 3, 2020

(65) Prior Publication Data

US 2020/0360658 A1 Nov. 19, 2020

Related U.S. Application Data

(60) Division of application No. 15/336,990, filed on Oct. 28, 2016, now Pat. No. 10,729,883, which is a (Continued)

(51) Int. Cl.
*A61M 25/01* (2006.01)
*A61M 25/04* (2006.01)
(Continued)

(52) U.S. Cl.
CPC ............ *A61M 25/01* (2013.01); *A61M 25/04* (2013.01); *A61N 1/056* (2013.01);
(Continued)

(58) Field of Classification Search
CPC .................. A61M 25/01; A61M 25/04; A61M 2025/0018; A61M 2025/09183;
(Continued)

(56) References Cited

U.S. PATENT DOCUMENTS 4,215,703 A 8/1980 Wilson
4,497,326 A 2/1985 Curry
(Continued)

FOREIGN PATENT DOCUMENTS

EP 0861676 A2 9/1998
EP 2197540 A1 6/2010
(Continued)

OTHER PUBLICATIONS

International Search Report and Written Opinion for PCT patent application PCT/US2009/048542, dated Sep. 30, 2009; 13 pages.
(Continued)

*Primary Examiner* — Diane D Yabut
(74) *Attorney, Agent, or Firm* — Mueting Raasch Group

(57) ABSTRACT

A lead delivery apparatus and a method of delivering a medical lead to an anatomic target site. The method includes inserting a hydraulic plug into an internal delivery lumen of a delivery shaft, and coupling a medical lead to the hydraulic plug. Hydraulic pressure is applied to the hydraulic plug through the delivery lumen, thereby moving the hydraulic plug toward an anatomic target site, and advancing the medical lead toward the target site.

19 Claims, 40 Drawing Sheets

Related U.S. Application Data continuation of application No. 12/570,044, filed on Sep. 30, 2009, now Pat. No. 9,480,839, which is a continuation-in-part of application No. 12/183,401, filed on Jul. 31, 2008, now Pat. No. 9,636,499, which is a continuation-in-part of application No. 12/495,844, filed on Jul. 1, 2009, now Pat. No. 8,229,572.

(60) Provisional application No. 61/182,205, filed on May 29, 2009, provisional application No. 61/076,183, filed on Jun. 27, 2008.

(51) Int. Cl.
*A61N 1/05* (2006.01)
*A61B 17/22* (2006.01)
*A61M 25/00* (2006.01)
*A61M 25/09* (2006.01)

(52) U.S. Cl.
CPC .............. *A61B 2017/22047* (2013.01); *A61B 2017/22048* (2013.01); *A61M 2025/0018* (2013.01); *A61M 2025/09183* (2013.01); *A61N 1/05* (2013.01); *A61N 2001/0585* (2013.01)

(58) Field of Classification Search
CPC ........... A61B 2017/22047; A61B 2017/22048; A61N 1/056; A61N 1/05; A61N 2001/0585

See application file for complete search history.

(56) References Cited

U.S. PATENT DOCUMENTS

| | | | |
|---|---|---|---|
| 4,619,246 A | 10/1986 | Molgaard-Nielsen et al. | |
| 5,003,990 A * | 4/1991 | Osypka | A61M 25/01 600/585 |
| 5,125,904 A | 6/1992 | Lee | |
| 5,147,377 A | 9/1992 | Sahota | |
| 5,167,239 A | 12/1992 | Cohen et al. | |
| 5,181,911 A | 1/1993 | Shturman | |
| 5,224,491 A | 7/1993 | Mehra | |
| 5,265,622 A | 11/1993 | Barbere | |
| 5,279,299 A | 1/1994 | Imran | |
| 5,295,958 A | 3/1994 | Shturman | |
| 5,312,355 A | 5/1994 | Lee | |
| 5,364,340 A | 11/1994 | Coll | |
| 5,409,463 A | 4/1995 | Thomas et al. | |
| 5,437,083 A | 8/1995 | Williams et al. | |
| 5,449,372 A | 9/1995 | Schmaltz et al. | |
| 5,456,667 A | 10/1995 | Ham et al. | |
| 5,456,705 A | 10/1995 | Morris | |
| 5,474,563 A | 12/1995 | Myler et al. | |
| 5,549,553 A | 8/1996 | Ressemann et al. | |
| 5,653,684 A | 8/1997 | Laptewicz et al. | |
| 5,693,014 A | 12/1997 | Abele et al. | |
| 5,735,869 A | 4/1998 | Fernandez-Aceytuno | |
| 5,741,320 A | 4/1998 | Thornton et al. | |
| 5,803,928 A | 9/1998 | Tockman et al. | |
| 5,833,707 A | 11/1998 | McIntyre et al. | |
| 5,902,331 A * | 5/1999 | Bonner | A61N 1/056 600/585 |
| 5,954,761 A | 9/1999 | Machek et al. | |
| 5,957,903 A | 9/1999 | Mirzaee et al. | |
| 6,010,498 A | 1/2000 | Guglielmi | |
| 6,014,589 A | 1/2000 | Farley et al. | |
| 6,033,413 A | 3/2000 | Mikus et al. | |
| 6,122,552 A | 9/2000 | Tockman et al. | |
| 6,152,946 A | 11/2000 | Broome et al. | |
| 6,161,029 A | 12/2000 | Spreigl et al. | |
| 6,196,230 B1 | 3/2001 | Hall et al. | |
| 6,259,938 B1 * | 7/2001 | Zarychta | A61B 5/6856 604/528 |
| 6,322,559 B1 | 11/2001 | Daulton et al. | |
| 6,331,190 B1 | 12/2001 | Shokoohi et al. | |
| 6,415,187 B1 | 7/2002 | Kuzma et al. | |
| 6,416,510 B1 | 7/2002 | Altman et al. | |
| 6,428,489 B1 | 8/2002 | Jacobsen et al. | |
| 6,595,989 B1 | 7/2003 | Schaer | |
| 6,602,271 B2 | 8/2003 | Adams et al. | |
| 6,662,045 B2 | 12/2003 | Zheng et al. | |
| 6,697,677 B2 | 2/2004 | Dahl et al. | |
| 6,928,313 B2 | 8/2005 | Peterson | |
| 6,931,286 B2 | 8/2005 | Sigg et al. | |
| 6,970,742 B2 | 11/2005 | Mann et al. | |
| 7,037,290 B2 | 5/2006 | Gardeski et al. | |
| 7,107,105 B2 | 9/2006 | Bjorklund et al. | |
| 7,171,275 B2 | 1/2007 | Hata et al. | |
| 7,344,557 B2 | 3/2008 | Yadin | |
| 7,765,014 B2 | 7/2010 | Eversull et al. | |
| 7,976,551 B1 | 7/2011 | Gutfinger et al. | |
| 8,229,572 B2 | 7/2012 | Drake et al. | |
| 8,394,079 B2 | 3/2013 | Drake et al. | |
| 8,920,432 B2 | 12/2014 | Drake et al. | |
| 2002/0077686 A1 | 6/2002 | Westlund et al. | |
| 2002/0147487 A1 | 10/2002 | Sundquist et al. | |
| 2002/0173835 A1 | 11/2002 | Bourang et al. | |
| 2003/0028234 A1 | 2/2003 | Miller et al. | |
| 2003/0088194 A1 | 5/2003 | Bonnette et al. | |
| 2003/0120208 A1 | 6/2003 | Houser et al. | |
| 2003/0204231 A1 | 10/2003 | Hine et al. | |
| 2003/0225434 A1 | 12/2003 | Glantz et al. | |
| 2003/0229386 A1 | 12/2003 | Rosenman et al. | |
| 2004/0059348 A1 | 3/2004 | Geske et al. | |
| 2004/0116878 A1 | 6/2004 | Byrd et al. | |
| 2004/0162599 A1 | 8/2004 | Kurth | |
| 2004/0215298 A1 | 10/2004 | Richardson et al. | |
| 2004/0242990 A1 | 12/2004 | Brister et al. | |
| 2005/0089655 A1 | 4/2005 | Lim | |
| 2005/0113862 A1 | 5/2005 | Besselink et al. | |
| 2005/0215990 A1 | 9/2005 | Govari | |
| 2006/0106445 A1 | 5/2006 | Woollett | |
| 2006/0210605 A1 | 9/2006 | Chang et al. | |
| 2006/0241737 A1 | 10/2006 | Tockman et al. | |
| 2006/0259063 A1 | 11/2006 | Bates et al. | |
| 2006/0292912 A1 | 12/2006 | Bjorklund et al. | |
| 2007/0016240 A1 | 1/2007 | Warnack et al. | |
| 2007/0043413 A1 | 2/2007 | Eversull et al. | |
| 2007/0079511 A1 | 4/2007 | Osypka | |
| 2007/0100409 A1 | 5/2007 | Worley et al. | |
| 2007/0100410 A1 | 5/2007 | Lamson et al. | |
| 2007/0250144 A1 | 10/2007 | Falk et al. | |
| 2008/0021336 A1 | 1/2008 | Dobak, III | |
| 2008/0065013 A1 | 3/2008 | Goodin | |
| 2008/0103537 A1 | 5/2008 | Sigg et al. | |
| 2008/0103575 A1 | 5/2008 | Gerber | |
| 2008/0183255 A1 | 7/2008 | Bly et al. | |
| 2008/0195226 A1 | 8/2008 | Williams et al. | |
| 2008/0300664 A1 | 12/2008 | Hine et al. | |
| 2009/0143768 A1 | 6/2009 | Parodi et al. | |
| 2009/0326551 A1 | 12/2009 | Drake et al. | |
| 2009/0326629 A1 | 12/2009 | Drake et al. | |
| 2009/0326630 A1 | 12/2009 | Tobin et al. | |
| 2010/0016863 A1 | 1/2010 | Drake et al. | |
| 2010/0016864 A1 | 1/2010 | Drake et al. | |
| 2010/0036473 A1 | 2/2010 | Roth | |
| 2015/0174394 A1 | 6/2015 | Drake et al. | |

FOREIGN PATENT DOCUMENTS

| | | |
|---|---|---|
| EP | 2344236 A2 | 7/2011 |
| WO | WO 2004/026371 A2 | 4/2004 |
| WO | WO 2005/053784 A2 | 6/2005 |
| WO | WO 2008/101078 A2 | 8/2008 |
| WO | WO 2009/158444 A1 | 12/2009 |
| WO | WO 2010/014413 A2 | 2/2010 |
| WO | WO 2010/014413 A3 | 4/2010 |
| WO | WO 2010/138648 A1 | 12/2010 |

OTHER PUBLICATIONS

International Search Report and Written Opinion for PCT patent application PCT/US2009/050783, dated Mar. 3, 2010; 15 pages.

(56) References Cited

OTHER PUBLICATIONS

International Search Report and Written Opinion for PCT patent application PCT/US2010/036280, dated Aug. 27, 2010; 9 pages.

* cited by examiner

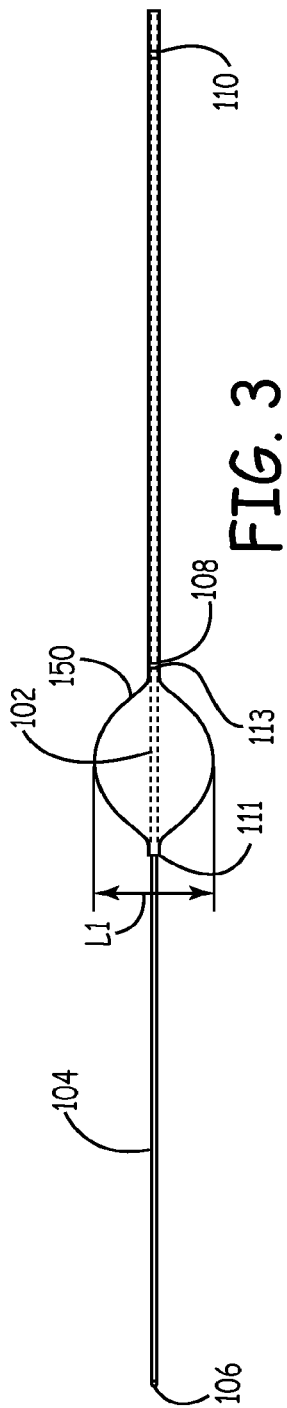
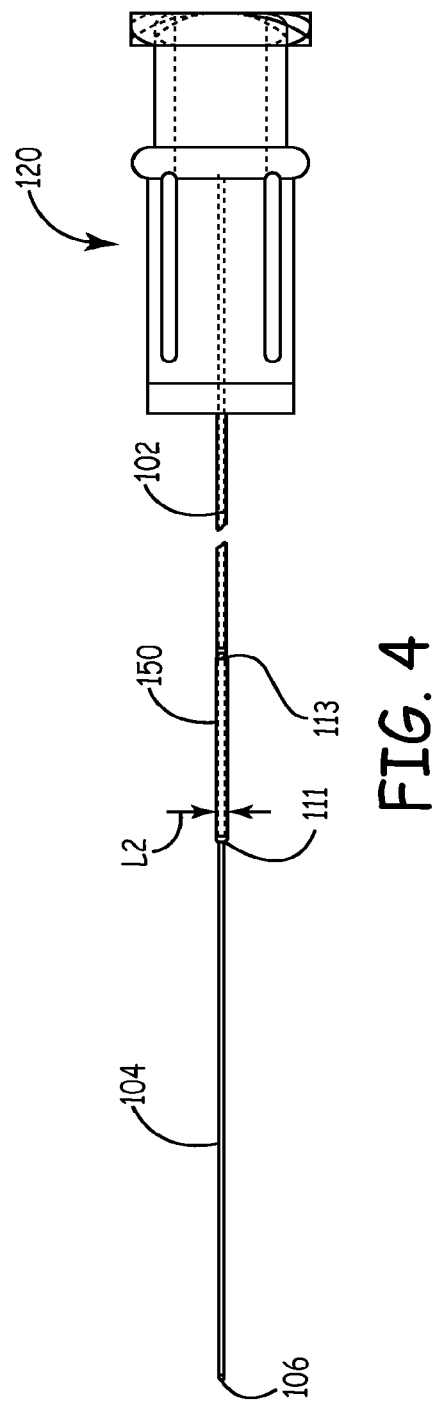

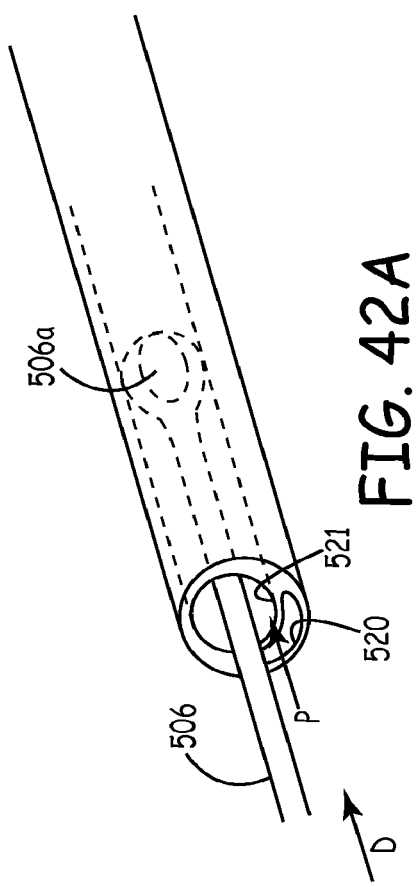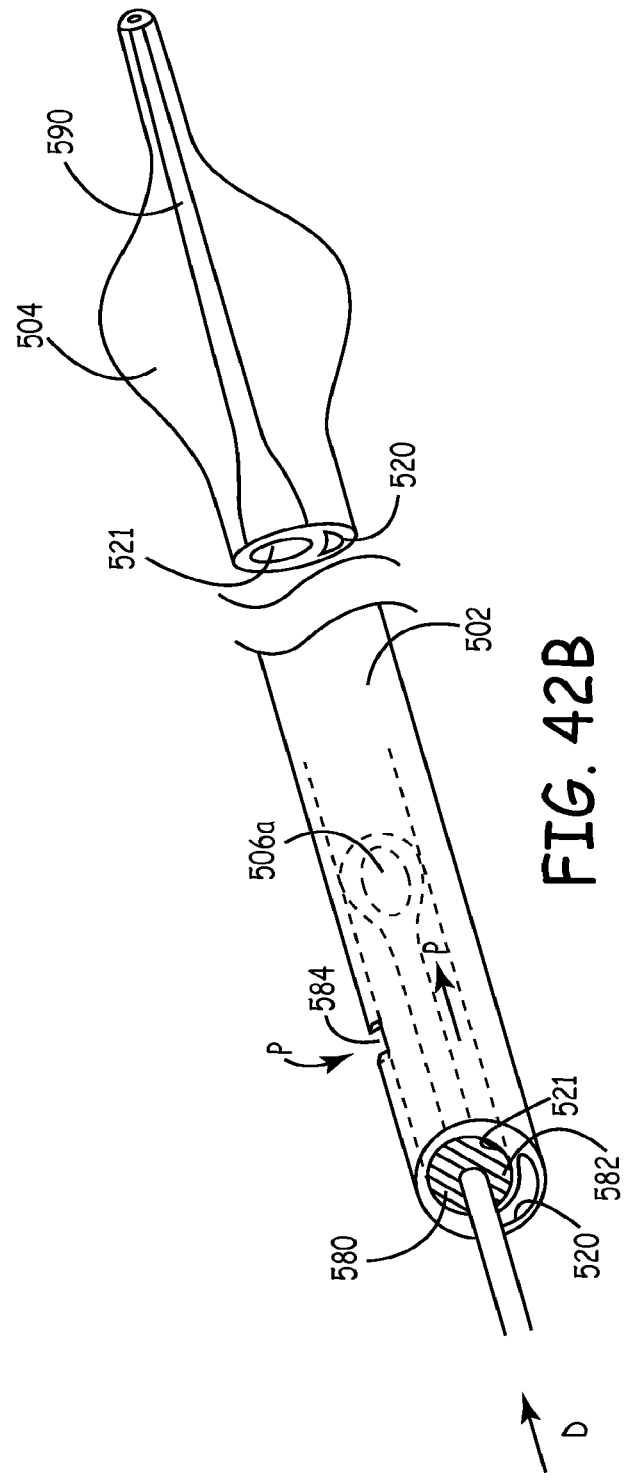

LEAD DELIVERY DEVICE AND METHOD

CROSS-REFERENCE TO RELATED APPLICATIONS

This application is a divisional of U.S. patent application Ser. No. 15/336,990, filed Oct. 28, 2016, which is a continuation patent application of U.S. patent application Ser. No. 12/570,044, filed Sep. 30, 2009, now U.S. Pat. No. 9,480,839, which is a continuation-in-part of U.S. patent application Ser. No. 12/183,401, filed Jul. 31, 2008, now U.S. Pat. No. 9,636,499, which claims the benefit of U.S. Provisional Application No. 61/076,183, filed on Jun. 27, 2008.

U.S. patent application Ser. No. 12/570,044, filed Sep. 30, 2009, is also a continuation-in-part of U.S. patent application Ser. No. 12/495,844, filed Jul. 1, 2009, which claims the benefit of U.S. Provisional Application No. 61/182,205, filed May 29, 2009.

This application is related to U.S. Ser. No. 12/183,105, filed Jul. 31, 2008, which claims the benefit of U.S. Provisional Application No. 61/076,183, filed on Jun. 27, 2008.

This application is related to U.S. patent application Ser. No. 11/468,910 filed on Aug. 31, 2006, which is a division of U.S. patent application Ser. No. 10/254,196, filed on Sep. 24, 2002, now U.S. Pat. No. 7,107,105.

The disclosures of the above applications are incorporated herein by reference.

INTRODUCTION

Various cardiac devices providing electrical stimulation, rhythm management, or resynchronization therapy to the heart include implantable electrically conductive leads in contact with excitable heart or other body tissue.

The present teachings provide a device and method for delivering an implantable electrically conductive lead to a target site for a use with a cardiac device.

SUMMARY

The present teachings provide a medical apparatus that includes an implantable electrically conductive lead for a cardiac device, the lead having an internal bore terminating at a distal lead opening, and a lead delivery device for delivering the distal end of the lead to a blood vessel during implantation of the lead. The lead delivery device includes a removably anchorable guidewire, and a fixator attached to a distal portion of the guidewire for anchoring the guidewire. The fixator is movable between a compact configuration and an expanded configuration. The fixator is capable of passing through the distal lead opening of the lead in the compact configuration. The fixator is capable of exerting a holding force in the range of about 0.89 to 4.45 N in the lumen of the blood vessel in the expanded configuration.

The present teachings also provide a medical method that includes inserting a distal end of cannulated catheter through cardiac tissue into a main cardiac vessel, attaching an expandable fixator to a distal portion of a guidewire, inserting the guidewire through the catheter, advancing the guidewire past the distal end of the catheter and into a target site in a lumen of a branching vessel, expanding the fixator into the target site, removably anchoring the fixator into the lumen with a holding force in the range of about 0.89 to 4.45 N, and removing the catheter. The method further includes advancing an implantable electrically conductive lead of a cardiac device over the guidewire to the target site without moving the guidewire while tensioning the guidewire, and delivering the distal portion of the lead at the target site.

In another aspect, the present teachings provide a medical apparatus that includes a cardiac device for providing cardiac therapy, or cardiac sensing, or a combination thereof, an implantable electrically conductive lead having proximal and distal ends, the proximal end couplable to the cardiac device, the lead having an internal bore terminating at a distal opening at the distal end, and a lead delivery device for delivering the distal end of the lead to a blood vessel during implantation of the lead. The lead delivery device includes a removably anchorable guidewire, and a fixator attached to a distal portion of the guidewire, the fixator movable between a compact configuration and an expanded configuration. The fixator has a compact width less or equal to about 0.483 mm and is capable of passing through the distal lead opening of the lead in the compact configuration. The fixator has an expanded width up to about 5 mm, and is capable of exerting a holding force in the range of about 0.89 to 4.45 N in the lumen of the blood vessel in the expanded configuration.

In a further aspect, the present teachings provide a medical apparatus comprising a guidewire and a fixator catheter. The fixator catheter comprises a tubular body with a distal portion and a proximal portion. The fixator catheter further comprises a distal opening, a fixator secured to the distal portion, and a body opening arranged between the fixator and the proximal portion. The guidewire is passed through the body opening and the distal opening of the fixator catheter. The fixator is movable between a compact configuration and an expanded configuration.

In yet another aspect, the present teachings provide a medical method comprising passing a guidewire through a fixator catheter. The fixator catheter comprises a tubular body with a distal portion and a proximal portion. The fixator catheter further comprises a distal opening, a fixator secured to the distal portion, and a body opening arranged between the fixator and the proximal portion. The guidewire is passed through the body opening and the distal opening of the fixator catheter. The method further comprises navigating the guidewire and fixator catheter to a desired site. At the desired site, the fixator is expanded to an expanded configuration in order to releasably secure the fixator catheter. An implantable electrically conductive lead of a cardiac device is advanced over the guidewire to the desired site while the fixator is deployed.

In various embodiments, the present teachings provide a lead delivery apparatus comprising an electrically conductive lead for an implantable medical device, a delivery shaft for delivering the lead to a target site, a fixator and a pulley structure. A flexible member is coupled to the delivery shaft and the lead and engages the pulley structure such that pulling a first portion of the flexible member moves the lead to the target site.

In various embodiments, the present teachings provide a method of delivering a medical lead to an anatomic target site. The method includes providing a delivery shaft and a fixator attached to a distal portion of the delivery shaft. The method also includes passing a flexible member having first and second ends through a longitudinal passage of the delivery shaft in a first orientation, around a pulley structure and out of the delivery shaft in a second direction substantially opposite to the first orientation such that a first end of the flexible member remains outside the deliver shaft. The method also includes inserting the lead delivery shaft loaded with the flexible member on a distal portion of the delivery shaft through cardiac tissue, fixating the fixator to a target site in a blood vessel, and coupling a lead over a portion of the flexible member associated with the second direction. Pulling the first end of the flexible member away from the proximal end of the delivery shaft in a first direction, advances the lead toward the target site in a second direction substantially opposite to the first direction.

In various embodiments, the method includes inserting a guidewire to cardiac target site, and providing a catheter with a fixator and a flexible member having first and second ends and coupled to a pulley structure. The method includes positioning the catheter over the guidewire and fixating the catheter at the target site with the fixator. The method also includes coupling a medical lead to the flexible member, pulling the first end of flexible member in a first direction away from the target site, and advancing the lead to the target site. The guidewire and the catheter are removed.

In various embodiments, the present teachings provide a method of delivering a medical lead to an anatomic target site. An elongated lead advancement member is coupled to a delivery shaft. The delivery shaft is inserted to the target site. The delivery shaft is temporarily attached to the target site using a fixator. A medical lead is inserted over the lead advancement member and pushed over the lead advancement member toward the target site.

In various embodiments, the method includes inserting a delivery shaft to the target site, coupling a medical lead to an elongated lead advancement member, slidably coupling the lead advancement member to the delivery shaft, and attaching the delivery shaft to the target site using a fixator. The elongated lead advancement member is pushed along the delivery shaft toward the target site, and the medical lead is advanced toward the target site.

In various embodiments, the method includes inserting a lead advancement member into a delivery lumen of a delivery shaft, threadably coupling the lead advancement member to a nut which is slidably and non-rotatably received in the delivery lumen, and coupling a medical lead to the nut. Rotating the lead advancement member advances the nut and the medical lead toward the target site.

In various embodiments, the method includes inserting a hydraulic plug into an internal delivery lumen of a delivery shaft and coupling a medical lead to the hydraulic plug. Applying hydraulic pressure to the hydraulic plug through the delivery lumen moves the hydraulic plug and the medical lead toward the target site.

In various embodiments, the method includes inserting a hydraulic plug into a first internal delivery lumen of a delivery shaft and coupling a medical lead to the hydraulic plug. Hydraulic pressure is applied to the hydraulic plug through a second delivery lumen which is separate from and substantially parallel to the first delivery lumen and communicates with the first delivery lumen through a U-shaped junction. The pressure moving the hydraulic plug, and advancing the medical lead toward the target site.

In various embodiments, the method includes inserting a hydraulic plug into an internal delivery lumen of a delivery shaft and coupling a medical lead to the hydraulic plug. Applying vacuum suction to the hydraulic plug through the delivery lumen moves the hydraulic plug and advances the medical lead toward the target site.

In various embodiments, the method includes inserting a medical lead into an internal delivery lumen of a delivery shaft, applying hydraulic pressure to an enlarged distal portion of the medical lead, and advancing the medical lead toward the target site.

The present teachings provide a lead delivery device. In various embodiments the lead delivery device includes a medical lead, an elongated delivery shaft insertable to an anatomic target site of a patient, and an elongated lead advancement member coupled to a ring. The ring slidably surrounds the delivery shaft. A flexible member outside the delivery shaft couples the medical lead to the ring such that pushing the lead advancement member toward the target site advances the medical lead toward the target site.

In various embodiments the lead delivery device includes a medical lead, an elongated delivery shaft insertable to an anatomic target site of a patient, and an elongated lead advancement member slidably received into a delivery lumen of the delivery shaft. A flexible member couples the medical lead to the delivery shaft such that pushing the lead advancement member toward the target site advances the medical lead toward the target site.

In various embodiments the lead delivery device includes a medical lead and an elongated delivery shaft insertable to an anatomic target site of a patient. The delivery shaft has a longitudinal delivery lumen communicating with a longitudinal open slot of the delivery shaft. An internally threaded nut is slidably received in the delivery lumen and includes an external tab slidably received in the longitudinal slot. An elongated lead advancement member threadably engages the nut through the delivery lumen of the delivery shaft. A flexible member coupling the medical lead to tab such that rotating the lead advancement member advances the nut and the medical lead toward the target site.

In various embodiments the lead delivery device includes a medical lead and an elongated delivery shaft insertable to an anatomic target site of a patient. The delivery shaft has a longitudinal delivery lumen communicating with a longitudinal open slot of the delivery shaft. A hydraulic plug is slidably received in the delivery lumen. A flexible member couples the medical lead to the hydraulic plug through the open slot, such that pressure exerted to the hydraulic plug through the delivery lumen advances the hydraulic plug and the medical lead toward the target site.

In various embodiments the lead delivery device includes a medical lead and an elongated delivery shaft insertable to an anatomic target site of a patient. The delivery shaft has a longitudinal delivery lumen with a closed channel cross-section. A hydraulic plug is slidably received in the delivery lumen. A flexible member couples the medical lead to the hydraulic plug such that pressure exerted to the hydraulic plug through the lumen advances the hydraulic plug and the medical lead toward the target site.

In various embodiments the lead delivery device includes a medical lead and an elongated delivery shaft insertable to an anatomic target site of a patient. The delivery shaft has a first longitudinal delivery lumen and a second longitudinal delivery lumen separate from and substantially parallel to the first delivery lumen and communicating with the first delivery lumen through a U-shaped junction. A hydraulic plug is slidably received in the first delivery lumen. A flexible member connecting the medical lead to the hydraulic plug and passing by a pulley structure therebetween, such that applying pressure through the second delivery lumen in a direction toward the target site moves the hydraulic plug in the opposite direction and advances the medical lead toward the target site.

In various embodiments the lead delivery device includes a medical lead and an elongated delivery shaft insertable to an anatomic target site of a patient. The delivery shaft has a longitudinal delivery lumen with a closed channel cross-section. A hydraulic plug is slidably received in the delivery lumen. A flexible member connects the medical lead to the hydraulic plug and passes by a pulley structure therebetween, such that applying vacuum suction through the delivery lumen in a direction away from the target site moves the hydraulic plug away from the target site and advances the medical lead toward the target site.

In various embodiments the lead delivery device includes an elongated delivery shaft insertable to an anatomic target site of a patient. The delivery shaft has a longitudinal delivery lumen and a side opening communicating with the delivery lumen. A medical lead has an enlarged distal portion and is inserted into the delivery lumen such that the enlarged distal portion is distal to the side opening. A flexible sealing member at the proximal end of the delivery shaft surrounds the medical lead such that applying pressure through the side opening advances the medical lead toward the target site.

In various embodiments, the lead delivery device includes a delivery shaft having a longitudinal lumen and a temporary fixator, a lead advancement member having a distal end, a connector coupling the distal end of the lead advancement member to the delivery shaft, and a medical lead coupled to the lead advancement member.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 3 is a plan view of a lead delivery device having a fixator according to the present teachings, the lead delivery device shown with the fixator in an expanded configuration;

FIG. 4 is a plan view of a lead delivery device having a fixator according to the present teachings, the lead delivery device shown with the fixator in a compact configuration;

FIG. 42A is a perspective view of a lead delivery device according to various embodiments of the present teachings;

FIG. 42B is a perspective view of a lead delivery device according to various embodiments of the present teachings;

Figure 1:
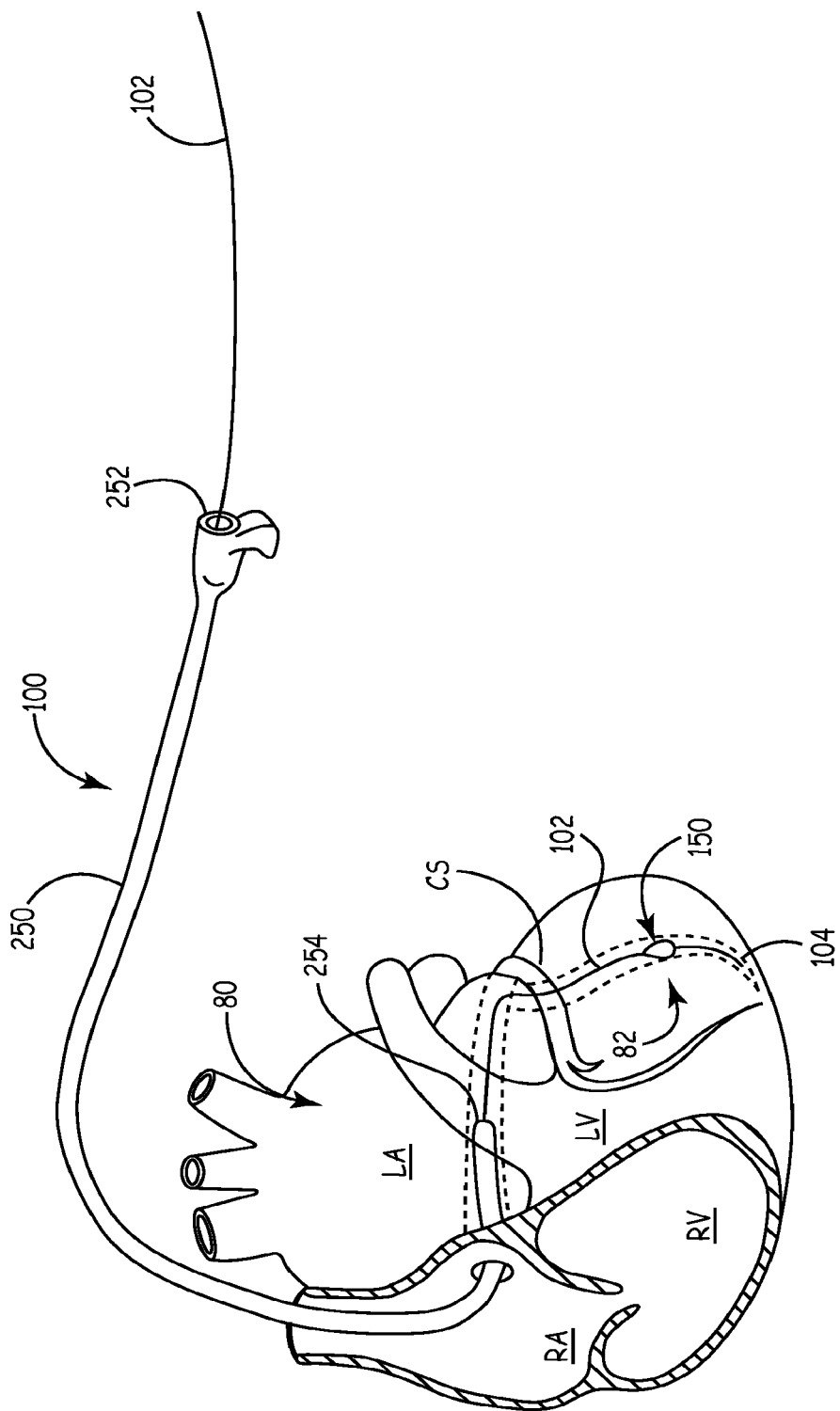
FIG. 1 is an environmental view of a lead delivery device according to various embodiments of the present teachings.

The drawings are not necessarily drawn to scale.

DESCRIPTION OF VARIOUS EMBODIMENTS

The following description is merely exemplary in nature and is in no way intended to limit the present teachings, applications, or uses. The present teachings are applicable to any devices that require implantation of electrically conductive leads, including pacemakers, defibrillators or other cardiac devices providing rhythm management, resynchronization therapy or other cardiac therapy.

During left heart (LH) lead delivery methods for implanting cardiac therapy devices, cannulated catheters can be used to provide support and stiffness and allow trackability of the lead into the coronary sinus and more acute branching vessels. For example, in Cardiac Resynchronization Therapy (CRT), a special third lead is implanted via the Coronary Sinus (CS) and positioned in a sub-selected cardiac vein to sense and/or pace the left ventricle in combination with atrial-synchronized, biventricular pacing using standard pacing technology. Following a sensed atrial contraction or atrial-paced event, both ventricles are stimulated to synchronize their contraction. The resulting ventricular resynchronization reduces mitral regurgitation and optimizes left ventricular filling, thereby improving cardiac function.

Guidewires can be used inside the Coronary Sinus and Great Cardiac Vein to gain access to acute side branches. A guidewire is placed into the targeted vessel and the lead is placed over the guidewire and through the catheter. Under existing methods, during lead delivery, a compressive force is maintained by a forward pressure on both the guidewire and lead to allow the lead to travel distally in the branching veins at the target site. The lead itself is designed to provide stiffness and steerability characteristics for the purpose of placement into the vessels. After the LH lead has reached its desired location, the delivery catheters used during the procedure must be removed by slitting because the proximal end of the lead is larger in diameter than the bore of the catheter and the catheter cannot be removed over the lead. The slitting procedure requires a very specific skill set, provides multiple avenues for user error and places constraints on catheter design, construction and use.

In contrast to the existing method described above, the present teachings provide a lead delivery device method that does not require slitting the catheter. The lead delivery device includes a guidewire that can be temporarily anchored in a sub-selected acute coronary vein branch during lead delivery. Fixation can be provided by a fixator that expands from a compact configuration of very low profile fitting inside a lead to an expanded configuration having a dimension large enough to allow sufficient tension to be placed on the guidewire to enable lead delivery over the guidewire in a zip-line or rope-climbing manner, as described below. The guidewire with the fixator in the compact configuration can be guided through the catheter to the target site. The catheter can then be removed before the lead is advanced over the guidewire. After the lead is implanted, the fixator is returned to the compact configuration and removed together with the guidewire through the implanted lead without slitting.

Figures 1A, 1B:
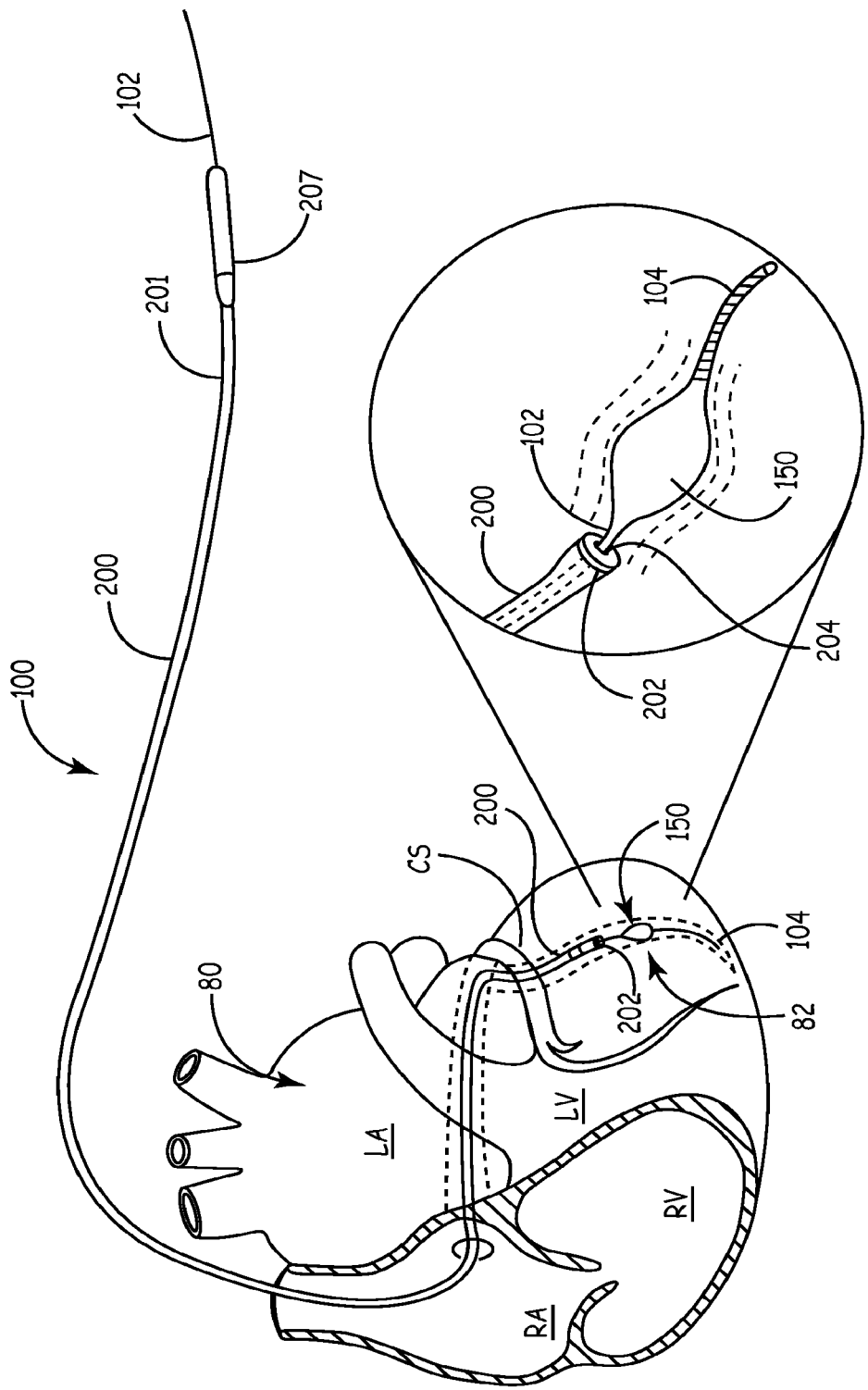
FIG. 1A is an environmental view of the lead delivery device of FIG. 1, shown in a second aspect.
FIG. 1B is an enlarged detail of the lead delivery device of FIG. 1B.
Figure 2:
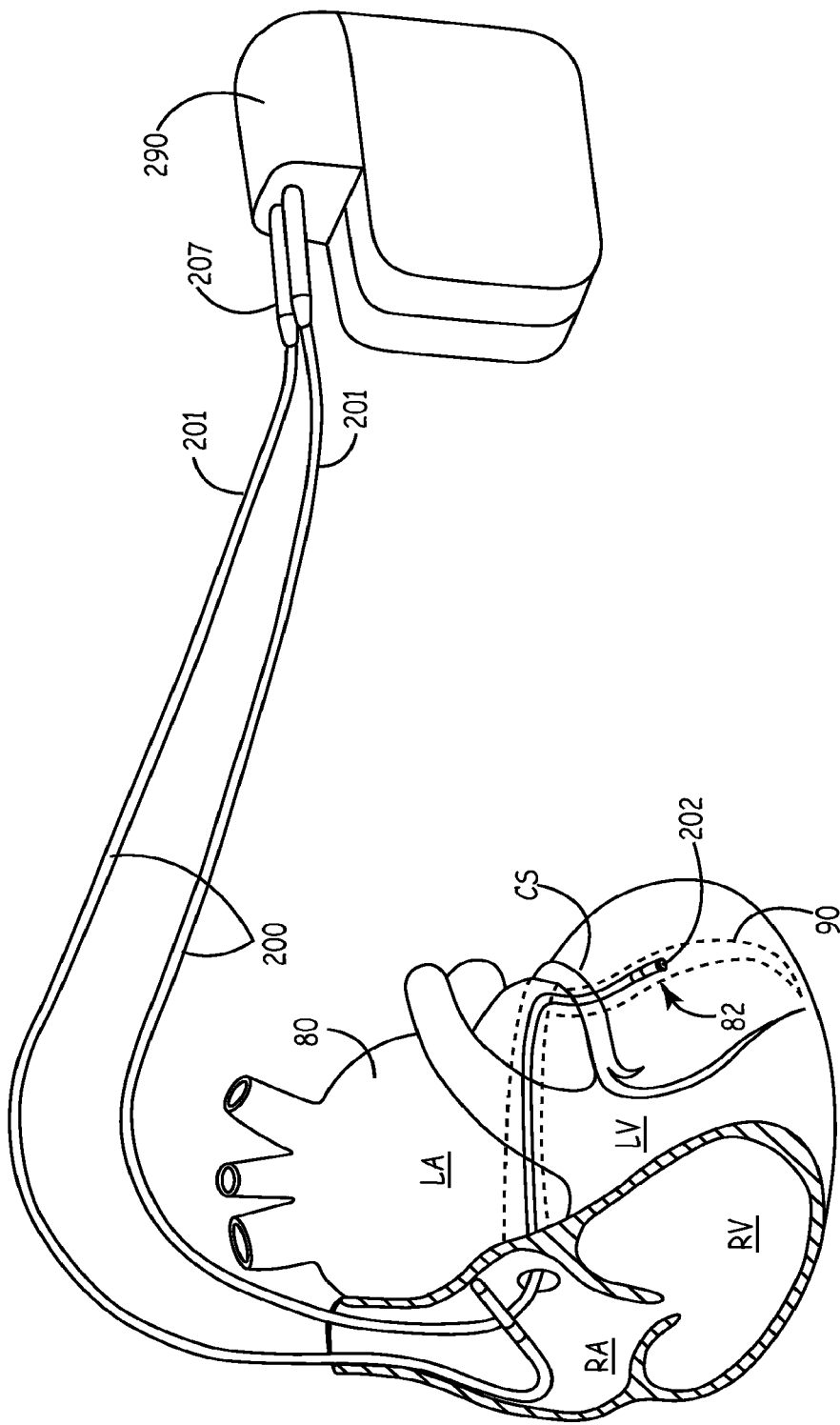
FIG. 2 is a perspective environmental view of the cardiac device with the lead implanted after the lead delivery device of FIG. 1B is removed.

An exemplary lead delivery device 100 according to the present teachings is illustrated during lead delivery of an electrically conductive lead 200 in FIGS. 1, 1A and 1B. An implanted lead 200 is shown in FIG. 2, after the lead delivery device 100 is removed. The lead 200 can be cannulated having an internal bore or lumen 204, a proximal portion 201, and a distal portion 202. The proximal portion 201 can be coupled with a connector pin 207 to a connector block of a cardiac device 290, with which the lead 200 is in electrical communication. A catheter 250 having a proximal end 252 and a distal end 254 can be used to insert the lead delivery device initially through heart tissue 80, as shown in FIG. 1.

The lead delivery device 100 can include a guidewire 102 entering a proximal end 252 of the catheter 250 and exiting through a distal end 254 of the catheter 250 as shown in FIG. 1. The guidewire 102 can be solid or cannulated with a bore 103, as shown in FIG. 12. The guidewire 102 can include a distal portion 104 terminating in a tip 106. The distal portion 104 can be flexible for ease in guiding the guidewire 102 through tortuous blood vessels to a target site 82, such as a branching vein branching off the coronary sinus or other main blood vessel. The lead delivery device 100 can include a fixator 150 coupled to the guidewire 102. The fixator 150 can assume an expanded or deployed configuration for anchoring the guidewire 102 near a target site 82 during lead delivery and implantation, as shown in FIGS. 3, and 5-11, illustrating various fixator aspects. Referring to FIG. 1, the catheter 250 can be removed by retracting the catheter 250 from heart tissue 80 after the lead delivery device is anchored at the target site 82. No slitting of the catheter 250 is required for removal of the catheter 250. After the catheter 250 is removed, the lead 200 can be guided over the guidewire 102 to the target site 82, as discussed further below.

The fixator 150 can be returned to a compact or undeployed configuration, such as the configuration illustrated in FIG. 4, for retracting and removing the guidewire 102 after lead delivery and implantation. The maximum dimension, diameter or width of the fixator 150 in the expanded configuration is denoted as L1 and in the contracted configuration as L2, as illustrated in FIGS. 3 and 4 for a fixator in the form of a balloon.

FIGS. 5-11 illustrate various fixators 150 in their expanded configuration showing the maximum dimension L1 for each fixator 150. The dimension L1 is selected to achieve a fixation force within a blood vessel of an amount that allows the guidewire 102 to be pulled in tension without being dislodged from the blood vessel while the lead is pushed over the guidewire 102, as discussed below. The fixation force F can be equal to or greater than about 2.24 N, or about 0.5 lbs, for achieving sufficient fixation within the blood vessel wall. The fixation force F can generally be in the range of about 0.89 to 4.45 N (or 0.2 to 1.0 lbs), depending on various factors, including the geometry of the branching vessel. The deployed width or dimension L1 corresponding to this fixation force F can be 5 mm, while the undeployed width or dimension L2 can be maintained to equal to or less than about 0.019 inches, or about 0.483 mm, to allow easy passage through commercially available leads, such as those used with medical devices available from Medtronic, Inc., of Minneapolis, Minnesota.

Figure 13:
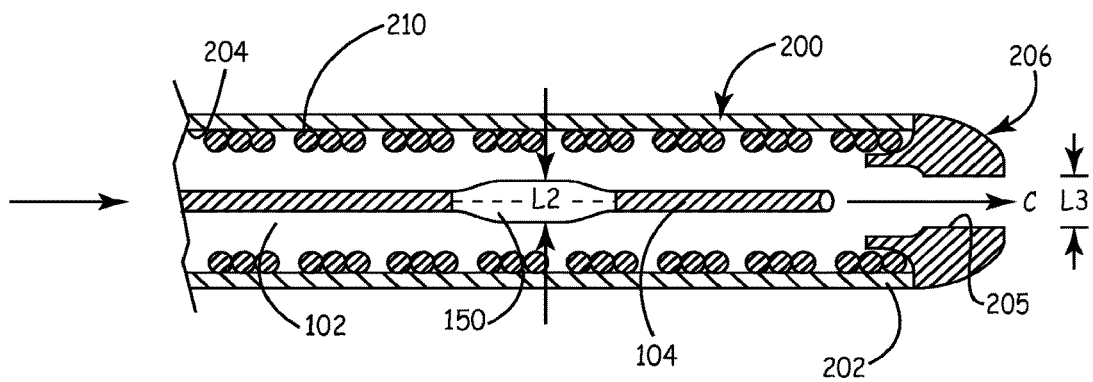
FIG. 13 is a sectional view of a lead delivery device according to the present teachings with a fixator in a compact configuration inside a lead.
Figure 14:
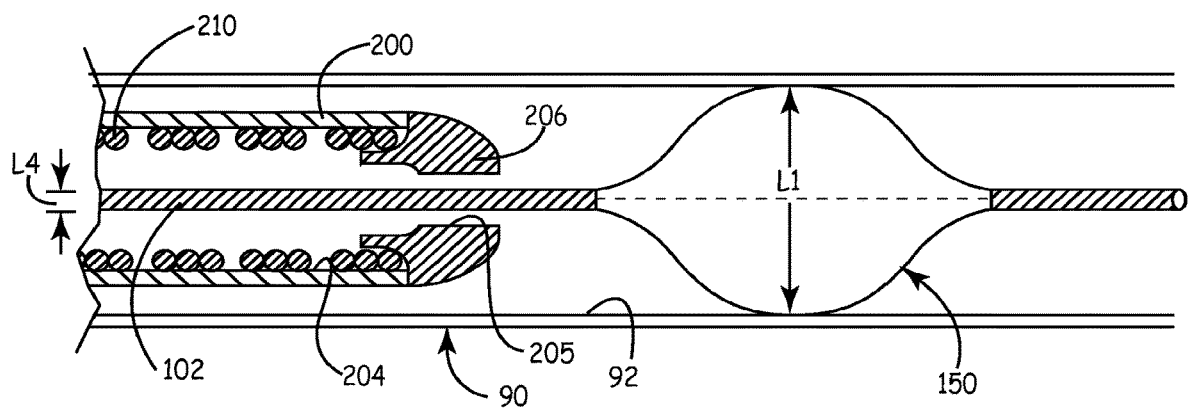
FIG. 14 is the lead delivery device of FIG. 13, shown with the fixator in an expanded configuration outside the lead.
Figure 15:
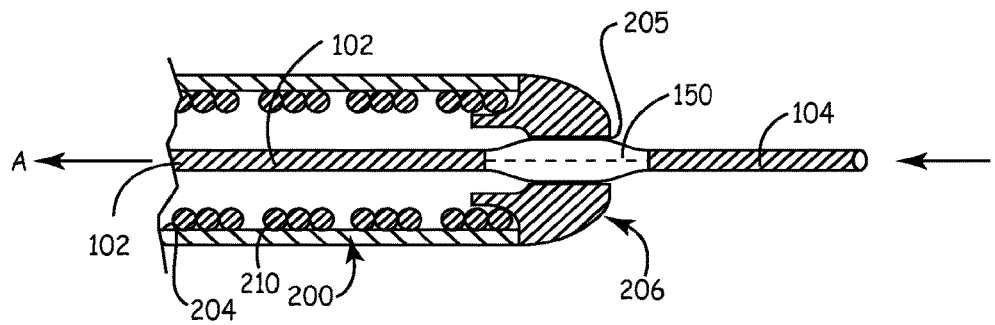
FIG. 15 is the lead delivery device of FIG. 13, shown with the fixator partially retracted inside the lead.

Referring to FIGS. 13-15, the distal portion 202 of an electrical lead 200 is illustrated in connection with a guidewire 102 having a width L4 and a fixator 150 having an undeployed width L2. The lead 200 is conductive and can deliver therapy in the form of electric energy at the target site 82. In one aspect, the lead 200 can also sense and relay information about electrical activity from the heart tissue 80 or target site 82 back to the cardiac device 290. The lead 200 can have an internal bore or lumen 204, an internal coil or other conductive element 210 and a tip portion 206 that can be an electrode tip with or without a seal. The tip portion 206 can define a distal opening 205 with width L3. In one aspect, the tip portion 206 can include a seal with flexible flaps, not shown. The guidewire width L4 can be about 0.346 mm (or about 0.014 inches) for providing steerability, stiffness and sufficient support for lead delivery over the guidewire 102.

Figure 16:
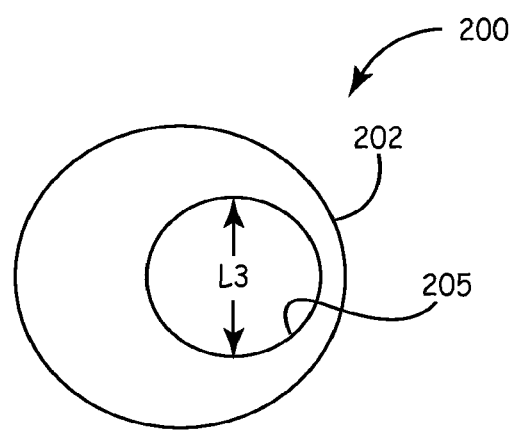
FIG. 16 is an end view of a distal end of an electrical lead with an offset distal opening.

The compact width L2 of the fixator 150 can be equal to or less than the width L3 of the distal opening 205, such that the fixator 150 can be pushed through the distal opening 205 in the direction C, as shown in FIG. 13. In one aspect the distal opening 205 can be offset relative to a central longitudinal axis of the lead 200, as shown in FIG. 16. The fixator 150 can be deployed to the expanded configuration within the blood vessel 90 such that the expanded width L1 of the fixator 150 can press against the internal lumen 92 of the blood vessel 90 with a holding force F, as discussed above, for temporarily anchoring the guidewire 102 into the blood vessel 90, as shown in FIG. 14.

Figure 5:
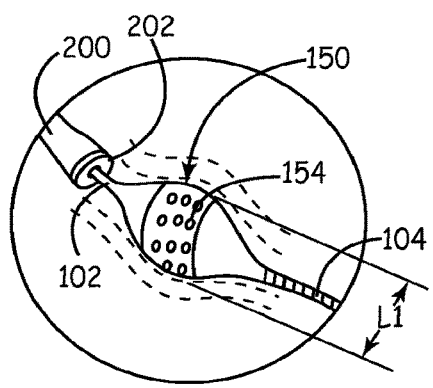
FIGS. 5-11 illustrate various fixators for a lead delivery device according to the present teachings.
Figure 7:
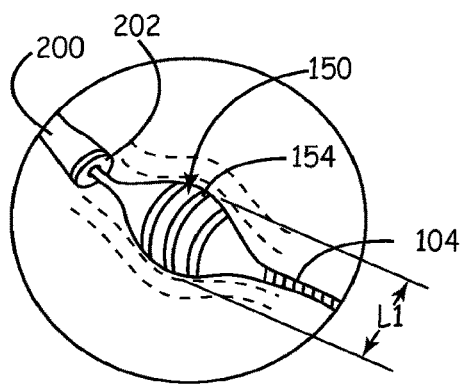

Various fixators 150 can be used to temporarily and removably anchor the guidewire 102 in the lumen 92 of a blood vessel 90. Referring to FIGS. 3 and 4, the fixator 150 can be a balloon having first and second ends 111, 113 attached to the guidewire 102. The balloon can be inflated, for example, with a gas or fluid, including a gel or other liquid, provided by a syringe through a valve 110 at a proximal end of the guidewire 102. In another aspect, a luer lock inflation port 120 can be coupled to the guidewire 102 for deploying the balloon. The balloon can be made from a polyblend material which is heated and stretched, placed around the guidewire 102 and bonded at first and second ends 111, 113 of the balloon onto the guidewire 102 with small amounts of cyanoacrylate adhesive, for example. A radio-opaque marker 108 in the form of a band can be placed adjacent the second (proximal) end 113 of the balloon for visualization during guided navigation. The radio-opaque marker 108 can also be in the form of a radio-opaque balloon coating or radio-opaque fluid filling the balloon. In another aspect, the balloon-type fixator 150 can include an etched fixation surface with etched surface fixation formations 154 in the form of bumps, rings, etc., as illustrated in FIGS. 5 and 7. In another aspect, the fixator 150 can be a balloon with spiral or helical or otherwise curved configuration for maintaining a percentage of blood flow through the blood vessel 90 and aiding fixation in tortuous anatomy.

Figure 9:
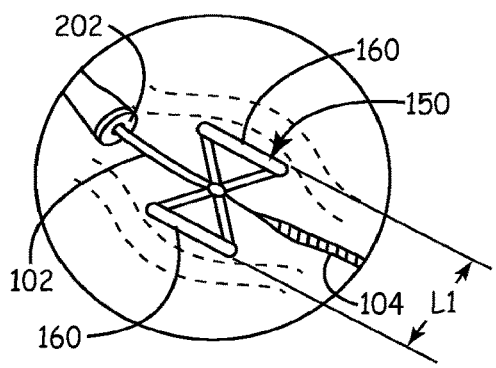
Figure 10:
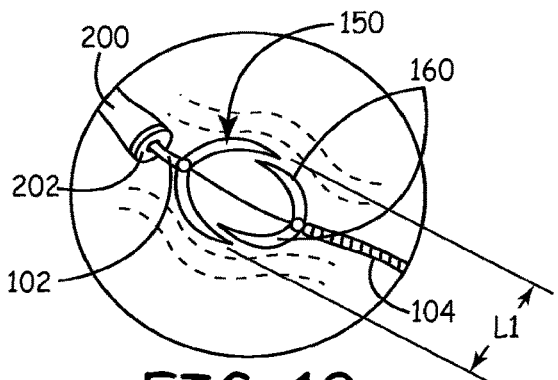
Figure 11:
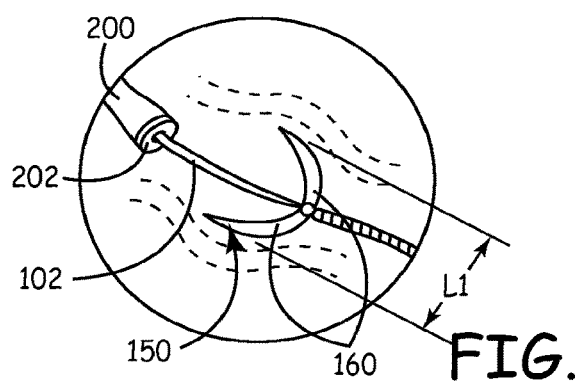
Figure 11A:
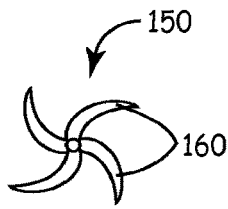
FIG. 11A is a top view of the fixator of FIG. 11.
Figure 12:
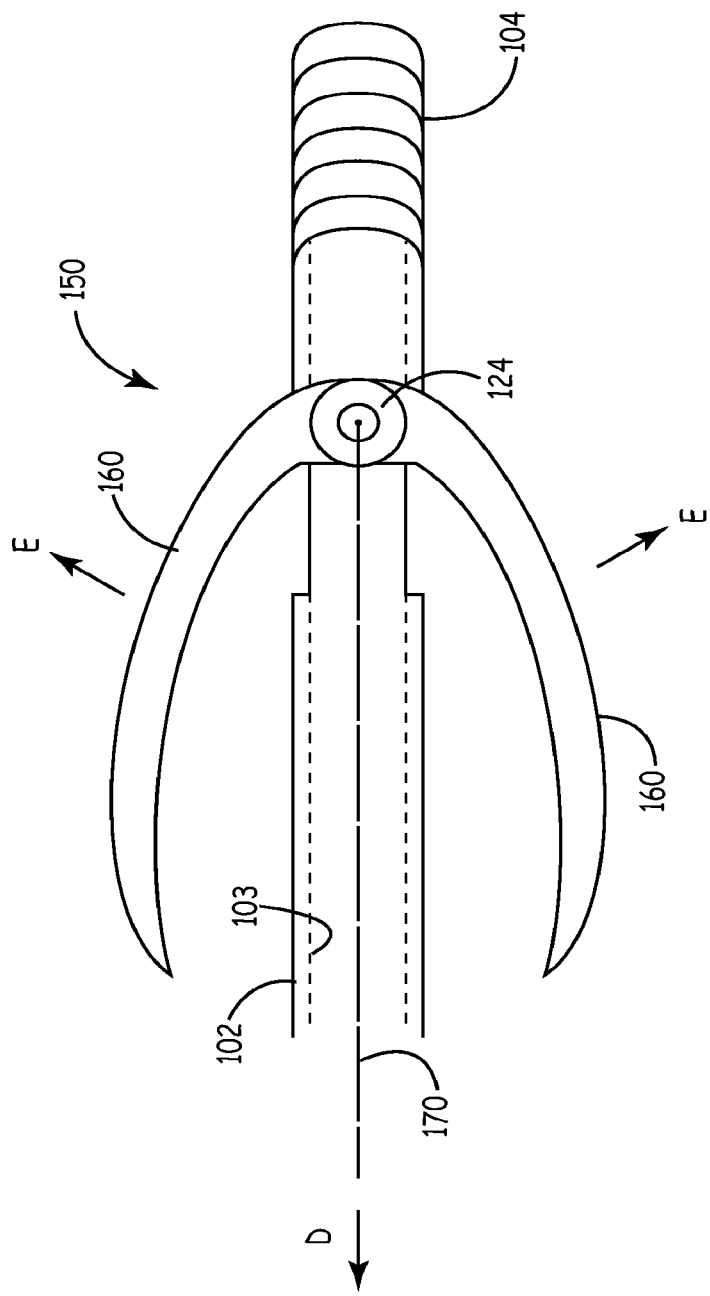
FIG. 12 is a side view of the fixator of FIG. 11, illustrating a deployment mechanism.

Referring to FIGS. 9-12, the fixator 150 can also be in the form of a mechanical anchor with deployable straight wings 160, as shown in FIG. 9, or curved wings 160, as shown in FIG. 10, or a pinwheel-type fixator 150, as shown in FIGS. 11 and 11A. The mechanical anchor 150 can be deployed with a longitudinal actuator 170 in the form of a wire or string or other elongated member passing through the bore 103 of a cannulated guidewire 102. Referring to FIG. 12, for example, the anchor wings 160 can pivot about a pivot pin 124 connected to the actuator 170 and can be deployed to the expanded position in the direction of arrows E by pulling the actuator 170 in the direction of arrow D. In other aspects, the fixator 150 can be in the form of a superelastic wire, such as nitinol, and can be pre-shaped to expand to an anchorable configuration within the blood vessel 90.

Figure 6:
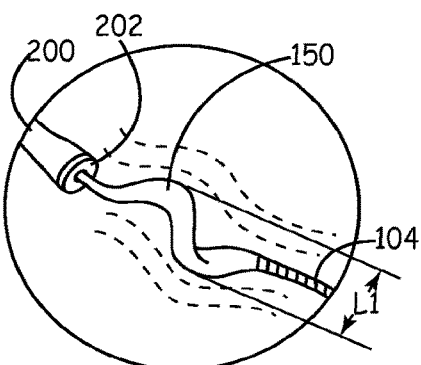
Figure 8:
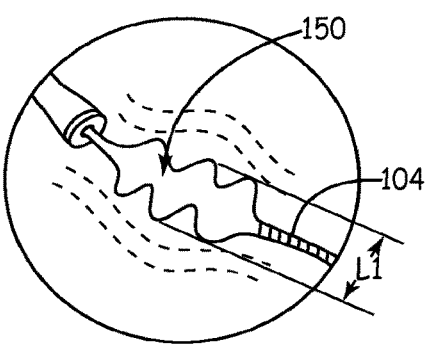

In another aspect, fixators 150 including polymer lobes or superelastic or memory-shape wire can be used. Further, the dimensions of the fixator 150, including the expanded width L1 and the compact width L2 can be selected to match the range of most common vessel sizes. The expanded shape of the fixator 150 can be selected to increase the contact area with the blood vessel and or provide multiple contact surfaces for increasing holding force and stability, as shown in FIGS. 6, 8, and 10, for example. The expanded shape can have a symmetric profile, as shown in FIG. 9, for example, or a non-symmetric profile, as shown in FIG. 6, for example. In other aspects, the expanded shape can have an asymmetric profile for anchoring unidirectionally rather than bi-directionally.

As discussed above, deployment of the fixator 150 and anchoring can occur after the cannulation of the coronary sinus CS with the catheter 250 and after sub-selection of a side branch with the guidewire 102. Further, fixation of the guidewire 102 by the expandable fixator 150 can be maintained during lead delivery and terminated after the lead 200 is delivered to the target vessel at the target site 82. At the discretion of the operating physician, fixation and release can occur multiple times during the medical procedure. Damage to the lead 200 during fixation can be avoided because fixator expansion and fixation occurs outside the lead 200.

It should be appreciated, that according to the present teachings the lead delivery device 100 with either a balloon or mechanical fixator 150 is configured and designed to function as a wedge or anchoring device for temporarily anchoring the guidewire 102 during the implantation of the electrical lead 200.

Referring to FIGS. 1-2, and 13-15, the cannulated catheter 250 can be inserted through heart tissue 80 into a coronary sinus CS, cardiac great vein or other main vessel stopping short of a target site 82 that is located in a sub-selected acute branching vessel 90. The guidewire 102 with the fixator 150 in the undeployed compact configuration can be inserted through the catheter 250, advanced past the distal end 254 of the catheter 250 through a main vessel to the target site 82 in the branching vessel 90, as shown in FIG. 1. The fixator 150 can then be deployed and become anchored in the lumen 92 of the branching vessel 90 with a holding force F, as discussed above. The catheter 250 can then be retracted and completely removed with no slitting procedure. The lead 200 can be guided over the anchored guidewire 102 until the distal portion 202 of the lead 200 reaches the target site 82, as shown in FIG. 1B. The lead 200 can be advanced by keeping the guidewire 102 in tension while pushing the lead 200 in the direction of the fixator 150. When the distal portion 202 of the lead 200 reaches the target site 82, the fixator 150 can be returned to its undeployed compact configuration and be retracted through the lumen 204 of the lead 200, as shown in FIG. 15. The lead 200 can remain installed in the target site 82, as shown in FIG. 2, or advanced more distally in the branching vessel 90 beyond the original target site 82 after the removal of the guidewire 102.

It will be appreciated that, in other aspects, the catheter 250 may be retained during the entire lead delivery procedure, such that the lead is inserted through the catheter 250 and over the guidewire 102, but in such cases slitting of the catheter 250 may not be avoided after lead implantation. In further aspects, the guidewire 102 and the lead 200 can be inserted through the catheter 250 in any order, i.e., guidewire 102 first, or lead 200 first or at the same time. In all aspects, however, the guidewire 102 can first be advanced to the target site 82 of a branching vessel 90 and the fixator 150 be deployed at the target site 82. Only then the distal portion 202 of the lead 200 is advanced to the target site 82 by pushing the lead 200 over the guidewire 102 toward the target site 82, while the guidewire 102 remains fixed. Specifically, the lead 200 can be advanced to the target site 82 in a climbing-like or zip line-like manner by pulling and tensioning the guidewire 102 while the guidewire 102 remains anchored with the deployed fixator 150 at the target site 82.

Figure 17:
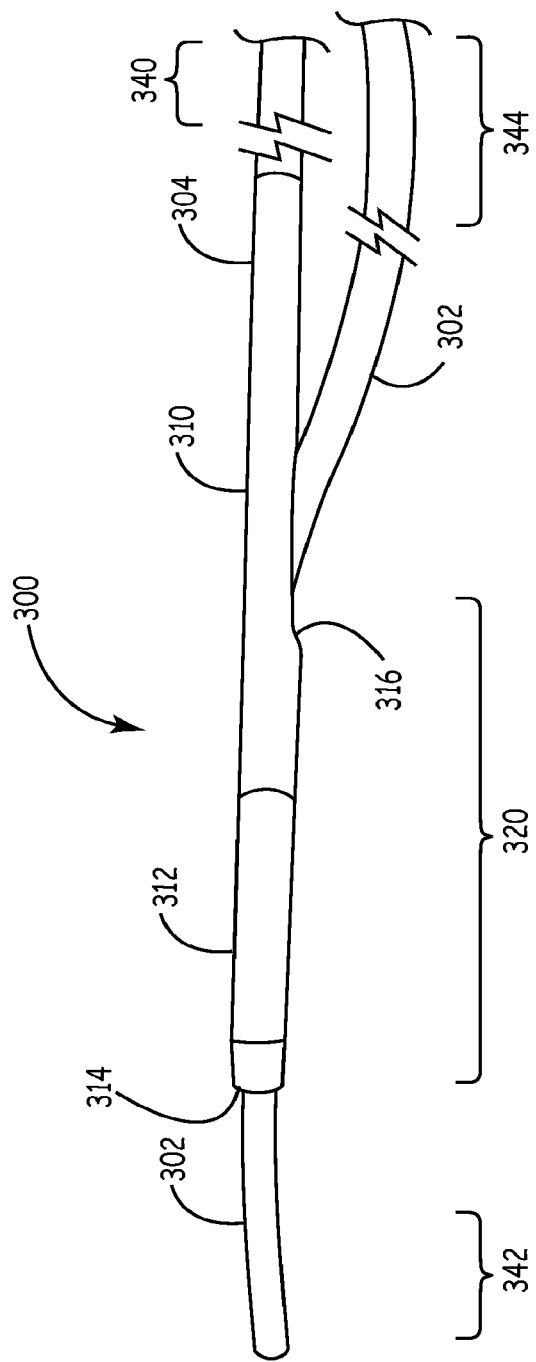
FIG. 17 is a plan view of a lead delivery device having a fixator according to the present teachings, the lead delivery device shown with the fixator in a compact configuration.

Referring now to FIG. 17, a lead delivery device 300 according to some embodiments of the present disclosure is illustrated. Lead delivery device 300 comprises a guidewire 302 and fixator catheter 304. Guidewire 302 may comprise a solid wire (as illustrated) or be cannulated, and includes proximal portion 344 and distal portion 342. The fixator catheter 304 is a cannulated catheter comprising a tubular body 310 with a distal portion 320 and proximal portion 340. A fixator 312 is secured on the distal end 320 of fixator catheter 304. In FIGS. 17-22, fixator 312 comprises an inflatable balloon, although any other form of fixator may be utilized, as described above.

Guidewire 302 passes through fixator catheter 304 such that the guidewire 302 is encased within the tubular body 310 in at least a portion of the distal portion 320 of the fixator catheter 304. In the illustrated embodiments, this is accomplished by passing the distal portion 342 of the guidewire 302 through the body opening 316 of fixator catheter 304 such that it extends through the distal opening 314. In this manner, the guidewire 302 and fixator catheter 304 are in communication at their distal portions 342, 320, while being separate at their proximal portions 344, 340.

Figure 18:
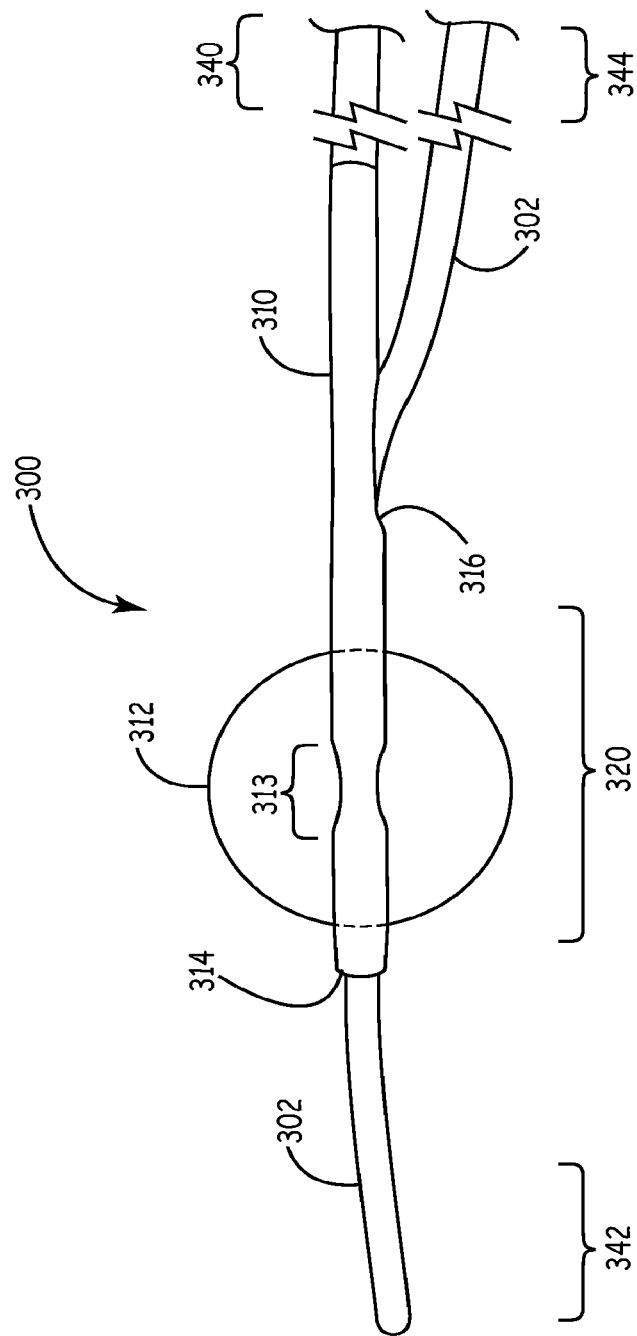
FIG. 18 is a plan view of a lead delivery device having a fixator according to the present teachings, the lead delivery device shown with the fixator in an expanded configuration.

Referring now to FIG. 18, lead delivery device 300 is shown in the condition where fixator 312 is expanded. In the illustration, fixator 312 comprises an inflatable balloon that may be expanded by a gas or fluid, as described more fully above. In some embodiments, the tubular body 310 of the fixator catheter 304 includes a lumen (not shown) that is in communication with the inflatable balloon 312 and proximal end 340. By providing a pressurized gas or fluid to the balloon 312, the fixator 312 is expanded to the expanded configuration. In the expanded configuration, the pressure inside balloon 312 will exert a force on a compressible or collapsible portion 313 of tubular body 310. In the illustrated embodiment, the compressible portion 313 is a portion of the lumen of the fixator catheter within the inflatable balloon, however, the compressible portion 313 may comprise a lumen of the balloon itself or other arrangement. The force exerted by inflatable balloon 312 on portion 313 of tubular body 310 will cause that portion 313 to compress guidewire 302 such that guidewire 302 is secured to fixator catheter 304. Portion 313 may be formed by providing a thinner wall in portion 313 than is utilized in the remainder of tubular body 310. Alternatively, portion 313 may be formed of a different material than that used to form the rest of tubular body 310, or any other alternative structure may be utilized (such as, adding a constrictive device or other securing mechanism). While the illustration in FIG. 18 shows an inflatable balloon 312 and a compressible or contract portion 313 of tubular body 310 to secure the guidewire 302 to fixator catheter 304, alternative structures and fixators may be substituted such that the guidewire 302 and fixator catheter 304 are secured together in the expanded configuration, while remaining independently movable in the compact configuration.

Figure 19:
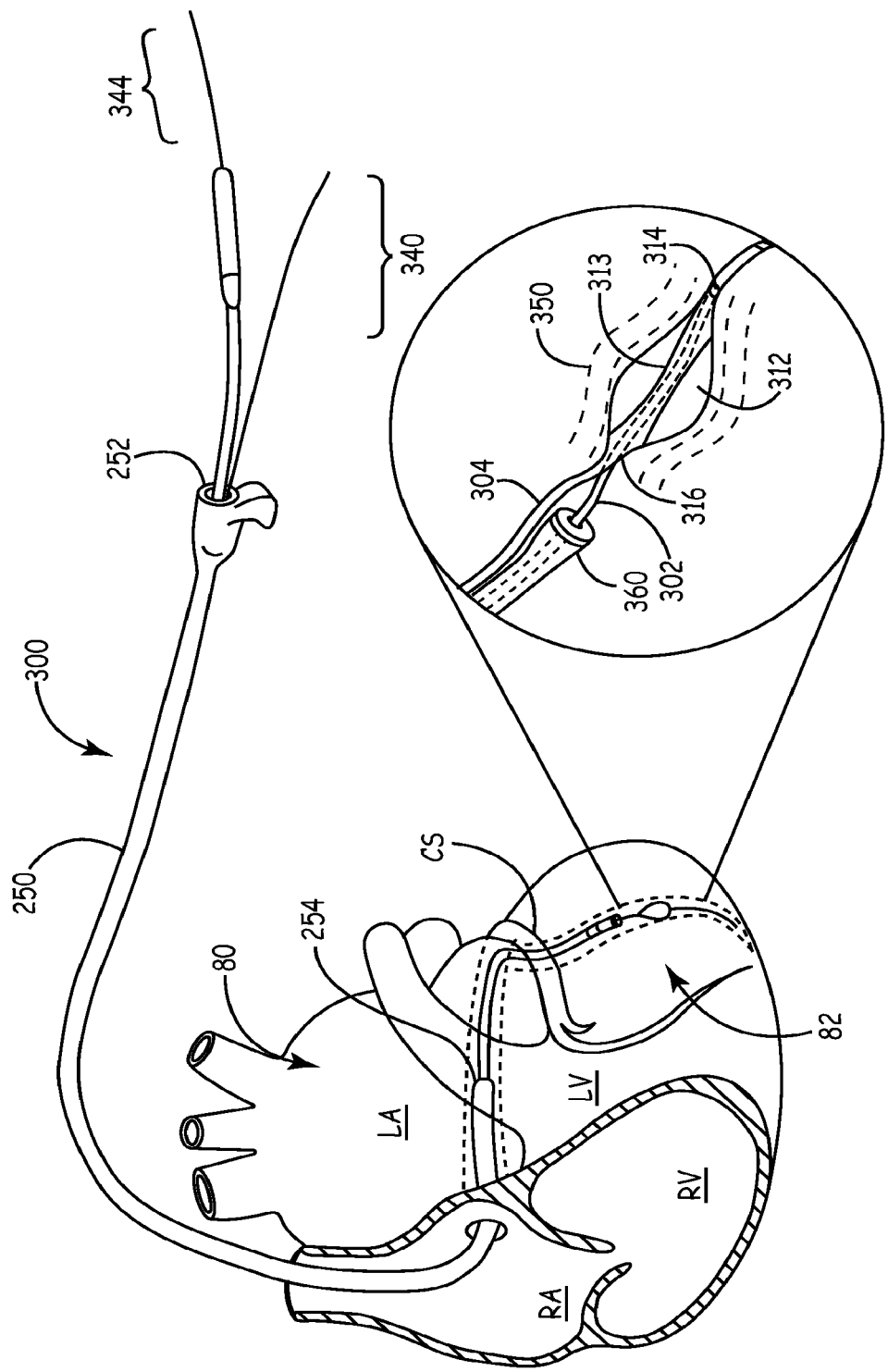
FIG. 19 is an environmental view of a lead delivery device according to various embodiments of the present teachings.
Figure 20:
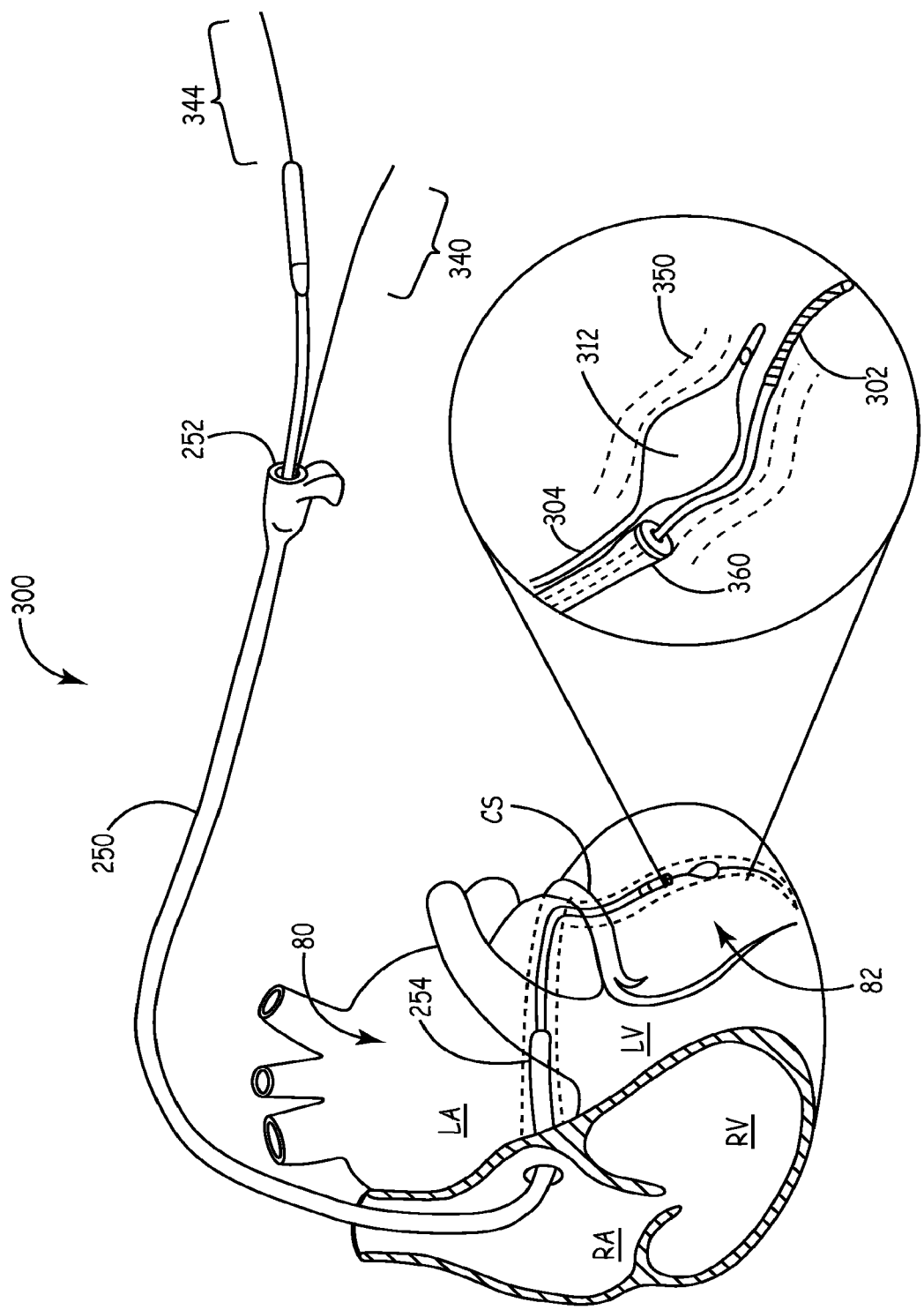
FIG. 20 is an environmental view of a lead delivery device according to various embodiments of the present teachings.

Referring now to FIGS. 19-22, a method for using lead delivery device 300 to implant an implantable electrically conductive lead 360 within a blood vessel 350 is illustrated. Similar to FIG. 1, FIGS. 19-20 show the lead delivery device 300 utilized to implant implantable electrically conductive lead 360 within the coronary sinus CS of heart tissue 80. A delivery catheter 250 having a proximal end 252 and distal end 254 may be utilized to assist in the delivery of guidewire 302 and fixator catheter 304 to a target or desired site 82. The fixator catheter 304, with guidewire 302 passed therein, is inserted through catheter 250 and navigated to a position within the desired site 82. Upon delivery to desired site 82, fixator catheter 304 deploys its fixator 312 to secure guidewire 302 and fixator catheter 304 within blood vessel 350. In the expanded configuration, fixator 312 exerts a force, as described above, upon the wall of blood vessel 350 sufficient to anchor both the guidewire 302 and fixator catheter 304 in the desired site 82 while delivery catheter 250 is removed and/or implantable electrically conductive lead 360 is delivered to desired site 82, e.g., via guidewire 302.

In the illustrations of FIGS. 19 and 20, delivery catheter 250 is shown as being present within the heart tissue 80 during delivery of lead 360. As shown in FIG. 19, in the expanded configuration fixator 312 compresses or collapses portion 313 of fixator catheter 304 such that guidewire 302 is fixedly secured within fixator catheter 304, as described more fully above. Alternatively, as shown in FIG. 20, guidewire 302 may be removed from fixator catheter 304 before fixator 312 is expanded. Fixator 312 may then be expanded to fixedly secure guidewire 302 between fixator 312 and the wall of blood vessel 350. Once guidewire 302 is fixedly secured within blood vessel 350, implantable electrically conductive lead 360 may be delivered to desired site 82 by, e.g., traveling over guidewire 302. With the guidewire 302 secured, the risk of the lead 360 being delivered incorrectly, i.e., outside of desired site 82, due to unintentional movement of guidewire 302 is reduced.

Once lead 360 is delivered to the desired site 82, the fixator 312 may be contracted to a compact configuration (as shown in FIG. 17, for example) and both guidewire 302 and fixator catheter 304 may be removed from desired site 82 and heart tissue 80. In some embodiments, fixator 312 may be utilized to secure lead 360 against blood vessel wall 350 while guidewire 302 is removed (see, e.g., FIG. 22). In this manner, it can be ensured that there is no unanticipated movement of lead 360 from desired site 82 while guidewire 302 is removed from the patient's body.

Figure 21:
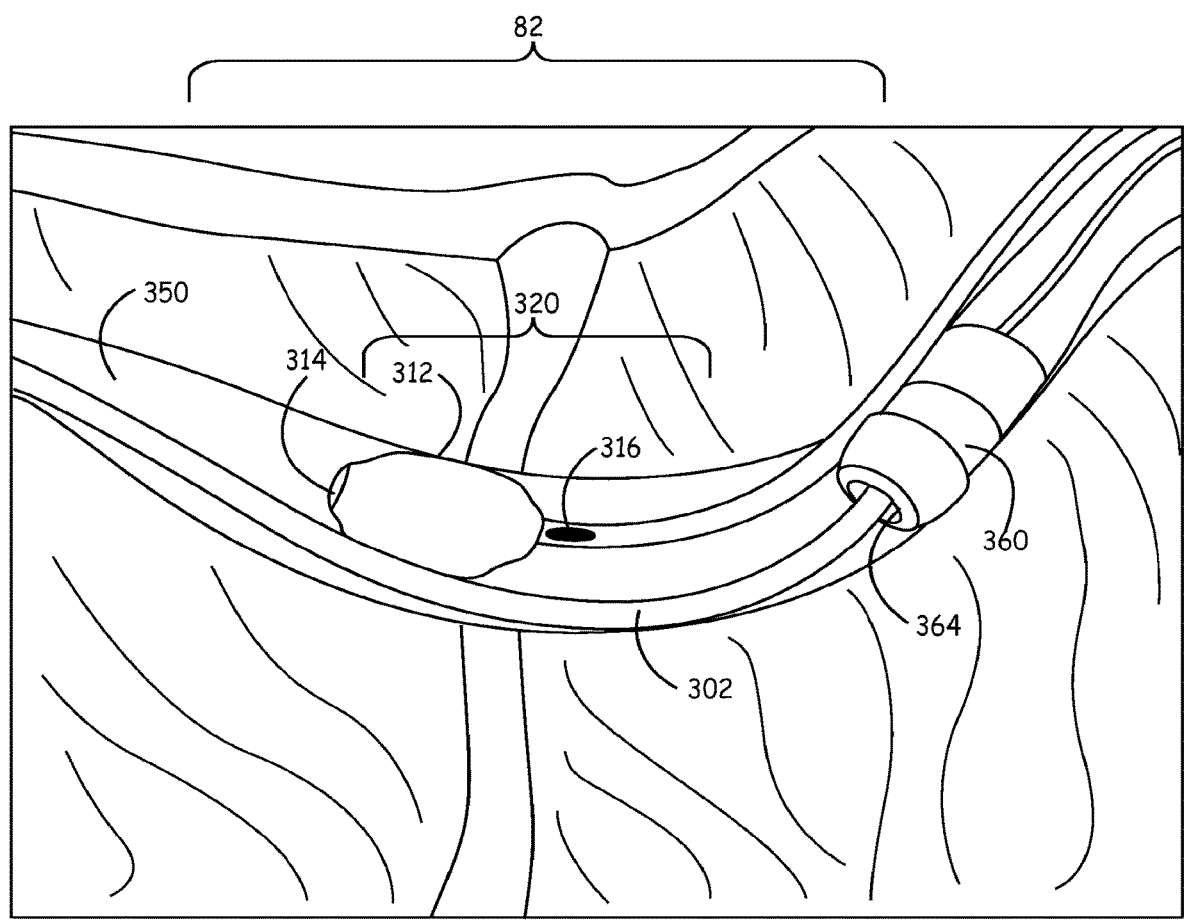
FIG. 21 is an environmental view of a lead delivery device according to various embodiments of the present teachings.
Figure 22:
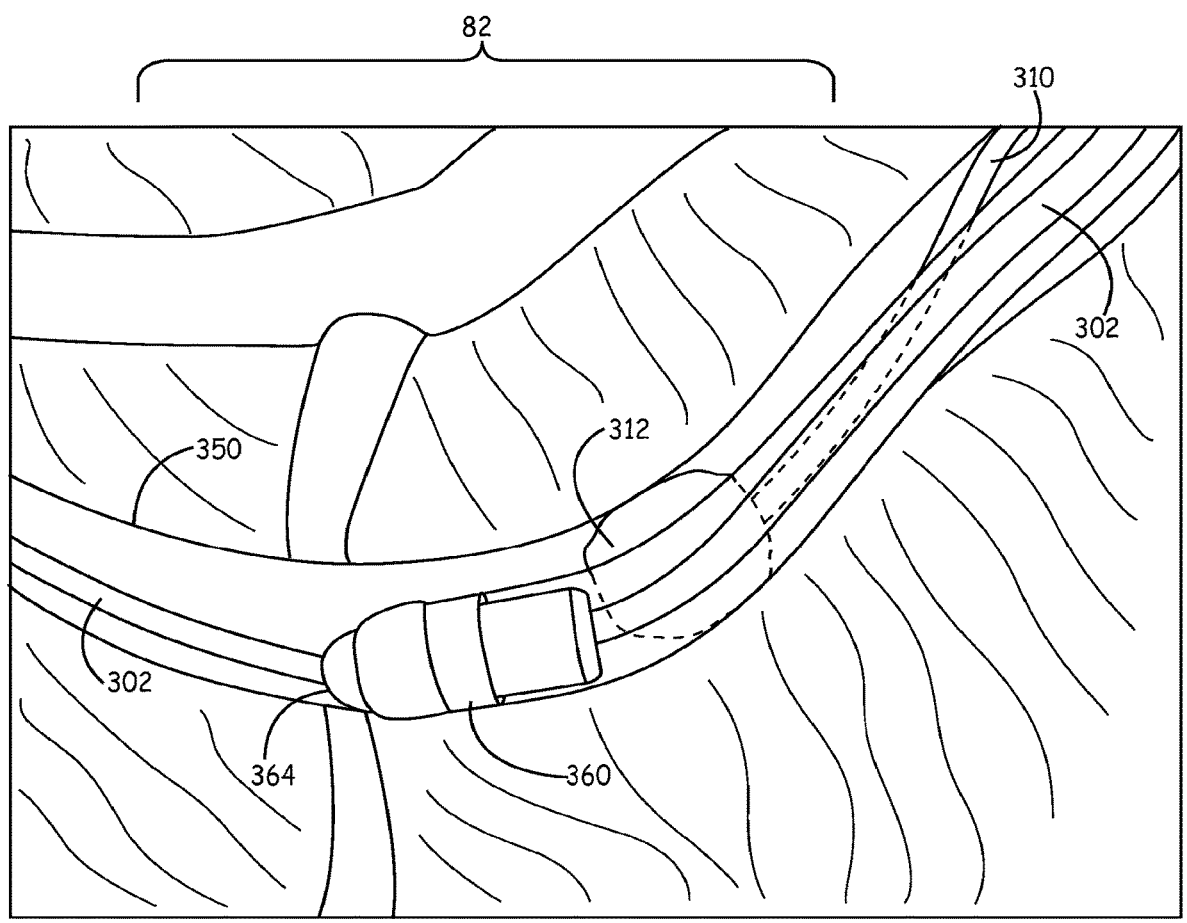
FIG. 22 is an environmental view of a lead delivery device according to various embodiments of the present teachings.

Referring now to FIGS. 21 and 22, a method of finely adjusting the position of guidewire 302 and lead 360 is illustrated. FIG. 21 shows fixator 312 in the expanded condition wherein guidewire 302 is secured between fixator 312 and the wall of blood vessel 350. This is accomplished, for example, by delivering lead delivery device 300 to the desired site 82 and then removing guidewire 302 from distal opening 314 and body opening 316 of fixator catheter 304. The guidewire 302 may be pulled out of communication with fixator catheter 304 by pushing on fixator catheter 304 until the distal portion 342 of guidewire 302 is pulled out of and exits body opening 316. Then, guidewire 302 may be pushed past the distal portion 320 of fixator catheter 304, as illustrated. Fixator 312 may be expanded to secure guidewire 302 against the wall of blood vessel 350 and implantable electrically conductive lead 360 can then be navigated to desired site 82 by, for example, traveling over guidewire 302 through opening 364.

The position of implantable electrically conductive lead 360 and guidewire 302 may be finely adjusted with the selective use of fixator catheter 304. Fixator 312 may be expanded to secure guidewire 302 (as shown in FIG. 21) such that the position of lead 360 may be adjusted. Alternatively, as shown in FIG. 22, fixator catheter 304 may be moved such that fixator 312 is immediately adjacent the body of lead 360. Fixator 312 may then be expanded to secure lead 360 within blood vessel 350. With lead 360 secured, the position of guidewire 302 may be adjusted without the possibility of moving lead 360. In this manner, a user may alternate between securing the guidewire 302 or lead 360 at a certain position, while adjusting unsecured lead 360 or guidewire 302, respectively, and thus more accurately and simply adjust the positioning of lead 360 within desired site 82.

Referring to FIGS. 23-32, a lead delivery device 400 and associated methods are illustrated according to various exemplary embodiments. The lead delivery device 400 can employ a method similar to pulley or flagpole principle to advance the lead using a pulley or pulley-like structure.

Figure 23:
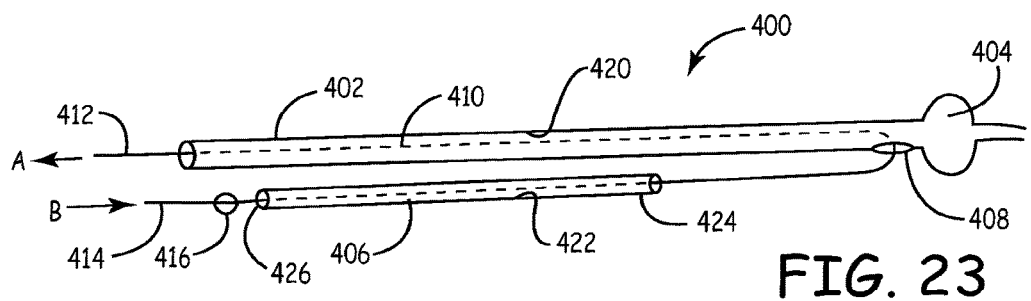
FIG. 23 is a diagrammatic view of a lead delivery device having a pulley-like structure according to various embodiments of the present teachings.
Figure 23A:
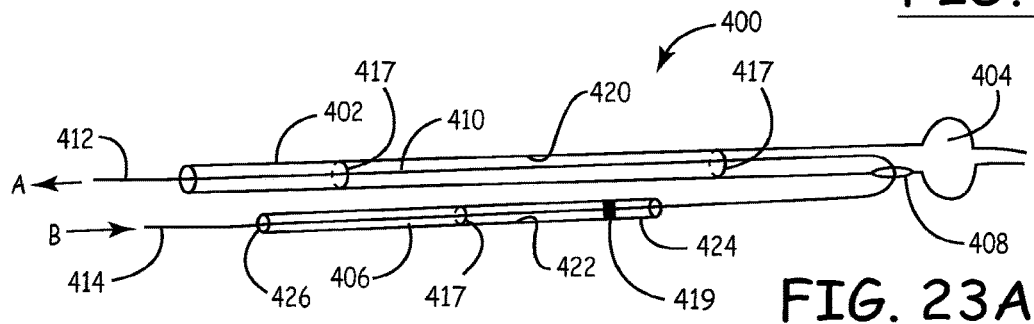
FIG. 23A is a diagrammatic view of a lead delivery device having a pulley-like structure according to various embodiments of the present teachings.

An exemplary embodiment of the lead delivery device 400 is illustrated in FIGS. 23 and 23A largely diagrammatically. The lead delivery device 400 can include a delivery shaft 402 having an inner passage or lumen 420, a fixator/fixation device 404 for temporary fixation during lead delivery and an electrically conductive medical lead 406 for an implantable medical device 290 (shown in FIG. 2). The medical lead 406 can have first and second ends 424, 426. The lead delivery device 400 can include a pulley structure 408 and an elongated flexible member 410, such as a string, rope or cable, having a first portion 412 and a second portion 414. The flexible member 410 can pass through the inner passage 420, change direction over or around the pulley structure 408 and pass through a lumen 422 of the lead 406, such that the flexible member 410 takes a U-shape by a U-turn at the pulley structure 408, as shown in FIG. 23. Pulling the first portion 412 of the flexible member 410 in the direction A moves the lead 406 in the direction B. A retainer, such as a knot, a button-like plate, a ball or a rod or other attachment device 416 can be at least temporarily coupled to the flexible member 410 and used as a stop to keep the lead 406 coupled onto the flexible member 410 as the flexible member 410 is pulled in the direction A away from heart tissue 80 to force the lead 406 to follow along the path of the flexible member 410.

Alternatively, as shown in FIG. 23A, the flexible member 410 can remain outside the delivery shaft 402 and outside the lead 406. The flexible member 410 can be coupled to the delivery shaft 402 with one or more external retainer elements 417, such as, for example, resilient rings, loose adhesive tape, easily breakable spot adhesive, or other devices that allow movement of the flexible member 410 relative to the delivery shaft 402, while maintaining coupling with the delivery shaft 402. Similarly, the flexible member 410 can be coupled to the lead 406 with one or more external retainer elements 417, or with one or more retainers 419 positioned adjacent to the distal end 424 of the lead 406.

The retainer 419 can be an attachment made by a dissolvable adhesive or by various other means, as discussed below. In various embodiments, the attachment can be made by electrical or thermal fusing. In various embodiments, the retainer 419 can include an electrical fuse such that passing a specified electrical current through the flexible member 410 can cause the electrical fuse to blow/break and release the flexible member 410 from the lead 406. A delivery shaft 402 and lead 406 of smaller diameter can be used when the flexible member 410 remains outside the delivery shaft 402 and the lead 406. It will be appreciated that the flexible member 410 need not extend along the entire length of the lead 406. The flexible member 410 can terminate, for example, at the location of the retainer 419, or the retainer 417, if used.

In various embodiments, the delivery shaft 402 can be made of a biocompatible material, such as, for example, a metallic or polymeric or other material. The delivery shaft 402 can also be a tubular catheter 402a or a tubular guidewire 402b or a solid guidewire 402c or other anchoring wire, as is discussed below in connection with FIGS. 24, 25 and 30-32. The lead 406 can travel along a path substantially parallel and adjacent to the shaft 402, either outside the passage 420 of the shaft 402, as illustrated in FIG. 23, or within the shaft passage 420. The flexible member 410 can be metal, polymer, string, plastic, hybrid of materials or can be made of different materials along the length of the flexible member 410.

The pulley structure 408 can be a pulley of appropriate size, such as a micro-machined pulley, or a 180-degree corner or U-turn in the delivery shaft 402 or outside the deliver shaft 402. In some embodiments, the pulley structure 408 can be formed by passing the flexible member 410 through first blood vessel 90 and exiting through a second blood vessel 90 forming a U-turn loop. Various exemplary embodiments are discussed below.

The fixator 404 can be an inflatable balloon, an expandable anchor, a distal portion of a catheter or guidewire that can be wedged in a small blood vessel because of its size, surface texture, friction, shape, properties, etc. The fixator 404 can also be selected from various fixators described herein above, such as fixators 150 or 312.

Figure 24:
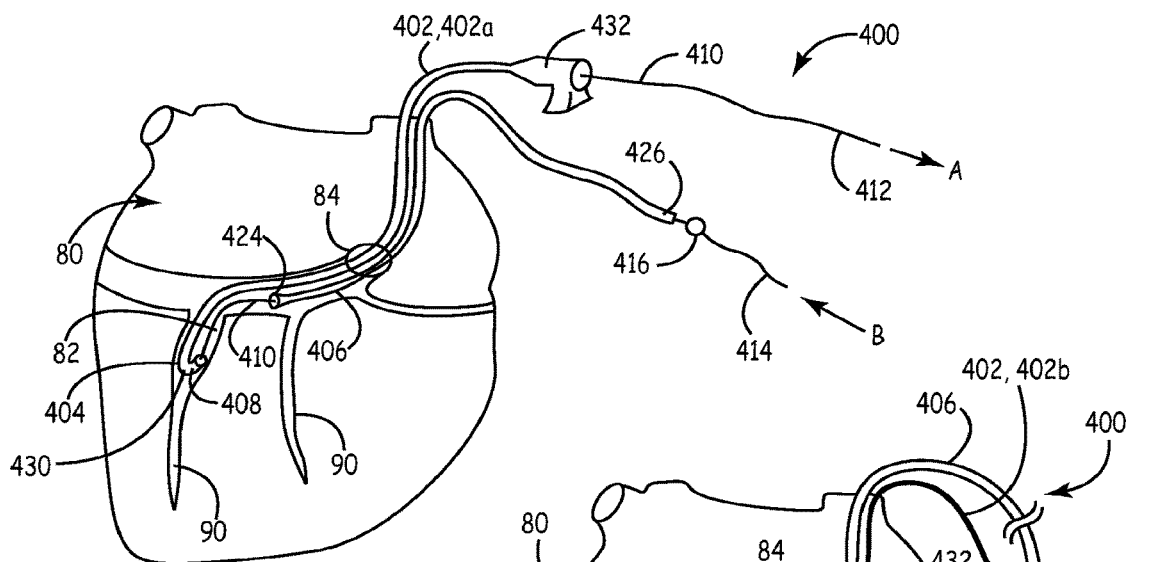
FIG. 24 is an environmental view of a lead delivery device according to various embodiments of the present teachings.
Figure 27:
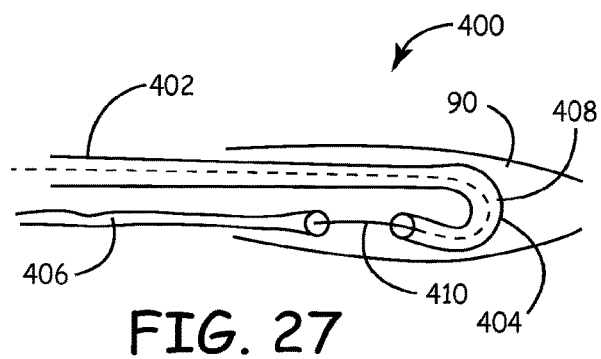
FIG. 27 is an environmental view of a lead delivery device according to various embodiments of the present teachings.

In various embodiments, the lead delivery device 400 can include a shaft 402 in the form of a flexible deformable catheter 402a, such as the fixator catheter 402a illustrated in FIG. 24. The catheter 402a or shaft 402 can be a hollow tubular member and can include a distal end 430 and a proximal end 432. In FIG. 24 the lead delivery device 400 is utilized to guide the lead 406 through the coronary sinus osteum 84 of heart tissue 80. The distal end 430 of the catheter 402a can be deformed to a U-shape within the blood vessel 90 and can function both as a fixator 404 and as a pulley structure 408 for delivering the lead 406, as is also illustrated in FIG. 27. Pulling the first portion 412 of the flexible member 410 in the direction A moves the lead 406 along the flexible member 410 in the direction B substantially parallel to the catheter 402a through coronary sinus osteum 84 until the first end 424 of the lead 406 reaches the target site 82. The flexible member 410 can then be removed by pulling at portion 414 in the opposite direction of arrow B. The catheter 402a can be removed by pulling the proximal end 432 away from the patient in the direction of arrow A.

Figure 25:
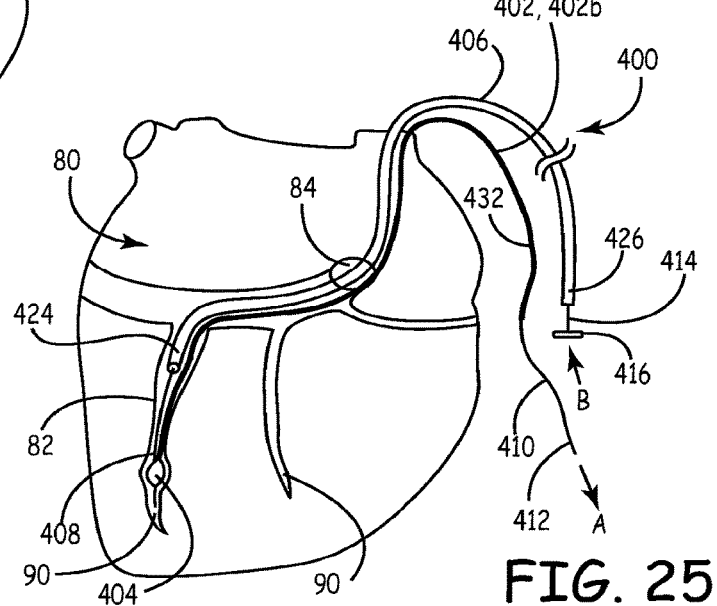
FIG. 25 is an environmental view of a lead delivery device according to various embodiments of the present teachings.

In various embodiments, the lead delivery device 400 can include a shaft 402 in the form of a flexible deformable guidewire 402b, as illustrated in FIG. 25. The guidewire 402b can be a hollow tubular member, generally of smaller diameter than the catheter 402a. In FIG. 25, the fixator 404 is illustrated as an expandable member, such as a balloon. The flexible member 410 can pass through the lumen of the guidewire 402b and form a U-turn at pulley structure 408, which can be any one of the pulley structures discussed above, including an opening in the fixator 404. In various embodiments, the guidewire 402b itself can function as both the delivery shaft 402 and the flexible member 410 with the fixator 404 removably attached to the unitary guidewire/flexible member, such that it remains at the target site 82 when the guidewire/flexible member is removed.

With continued reference to FIG. 25, pulling the first portion 412 of the flexible member 410 in the direction A moves the lead 406 along the flexible member 406 in the direction B substantially parallel to the guidewire 402b through coronary sinus osteum 84 until the first end 424 of the lead 406 reaches the target site 82. The flexible member 410 can then be removed by pulling at portion 414 in the opposite direction of arrow B. The guidewire 402b can be removed by pulling the proximal end 432 away from the heart tissue 80 in the direction of arrow A.

Figure 26:
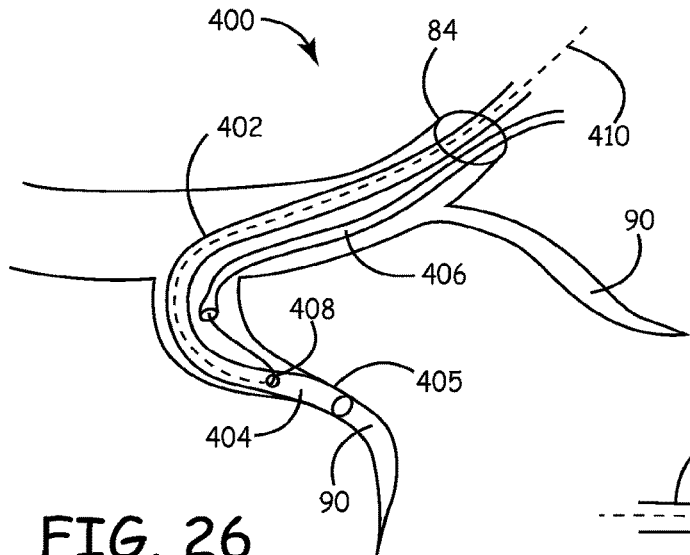
FIG. 26 is an environmental view of a lead delivery device according to various embodiments of the present teachings.

In various embodiments, the lead delivery device 400 can include a shaft 402 having a distal portion 405 with stiffness and width configured to form a fixator 404 by frictional attachment to the blood vessel 90, as illustrated in FIG. 26. In the illustrative embodiment of FIG. 26, the pulley structure 408 is a hole through which the flexible member 410 exits the delivery shaft 402, makes a U-turn and passes through the lumen of the lead 406.

Figure 28:
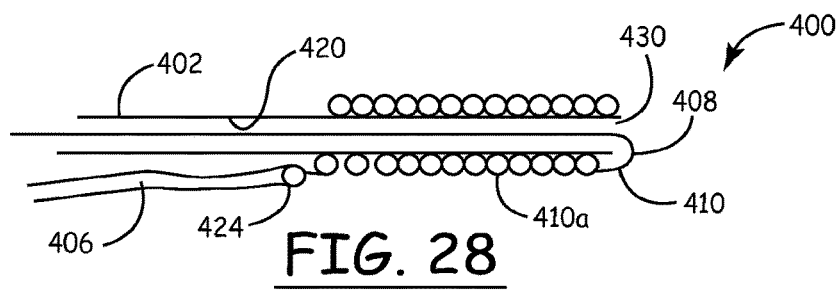
FIG. 28 is a detail of an environmental view of a lead delivery device according to various embodiments of the present teachings.

In various embodiments, a portion 410a of the flexible member 410 can include a coiled portion 410a coiled around a portion of the delivery shaft 402 between the distal end 424 of the lead 406 and a distal end 430 of the shaft 402, as illustrated in FIG. 28. The coiled portion 410a can keep the lead 406 close to the delivery shaft 402 as the lead 406 is moved along the shaft 402. The coiled portion 410a moves in translation with the lead 406 and unravels as the flexible member enters the passage 420 of the delivery shaft 402 at the distal end 430 of the delivery shaft 402 where the flexible member 410 forms the pulley structure 408 by a U-turn.

Figure 29:
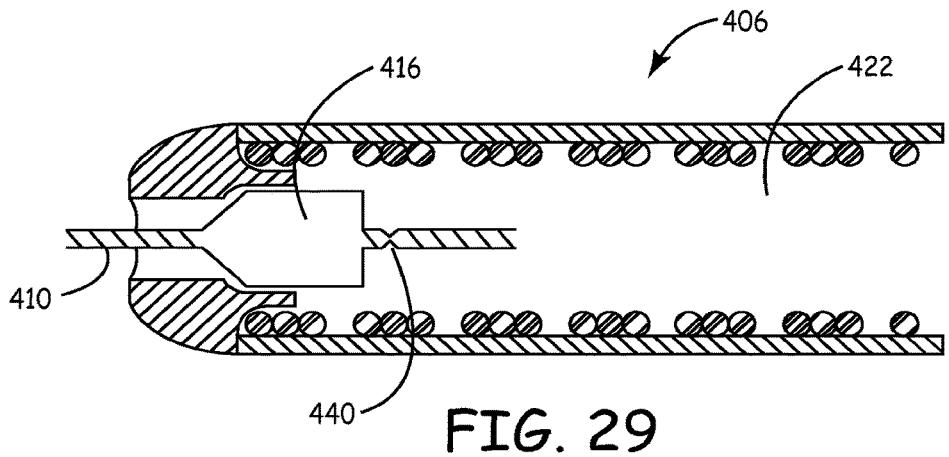
FIG. 29 is a sectional view of a lead with an internal attachment device for a lead delivery device according to various embodiments of the present teachings.

In various embodiments, the various retainers 416, 417, 419 described above can be coupled to the flexible member 410 outside the lead 406, as shown in the exemplary illustrations of FIGS. 23-25. In various embodiments, the retainer 416 can be coupled to the flexible member 410 within the lumen 422 of the lead 406, as illustrated in FIG. 29. The retainer 416 can be, for example, a knot in the flexible member 410, a metallic or polymer device, a wedge, an inflatable device, a deformable device, or an expandable basket. The retainer 416 can be temporarily shapeable or can be made of a memory-shaped device. The retainer 416 can also be a threaded screw or a device held in the lumen 422 of the lead by compression fit. The retainers 416, 419 can be attached to flexible member 410 and/or the lead 406 by electrical connection, by adhesive, by thermal connection (heating or freezing). The retainers 416, 419 can be detached and disconnected by softening an adhesive, by dissolving, by electrically breaking a fuse embedded in the retainer as described above in connection with retainer 419, by mechanical force to overcome the attachment force, such as by breaking the flexible member 410 or a portion of the lead 406, or by deforming, deflating, or breaking the retainer 416. A section of reduced width or a section weakened with a notch or other frangible feature 440 may be provided at selected location. In various alternative embodiments, the retainer 416 can be removed by pulling the flexible member 410 in a direction opposite to the direction B, as shown in FIGS. 24 and 25.

Figure 30:
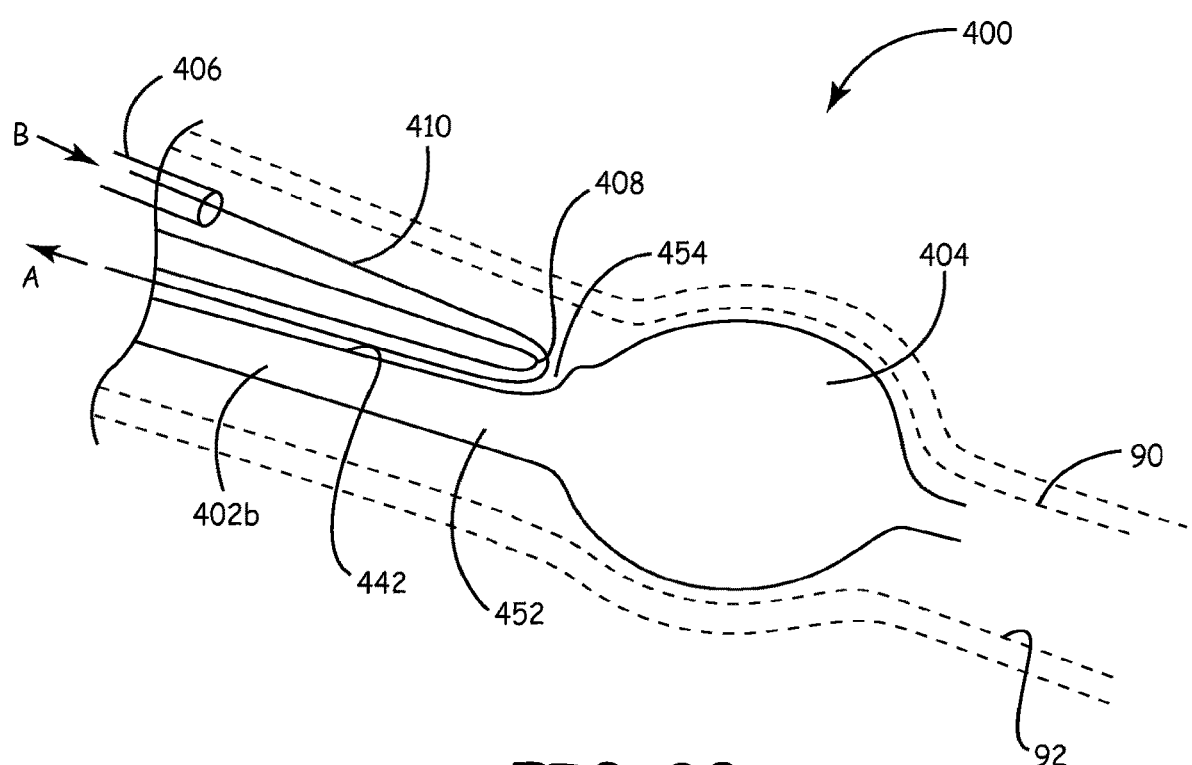
FIG. 30 is an environmental view of a lead delivery device according to various embodiments of the present teachings.
Figure 31:
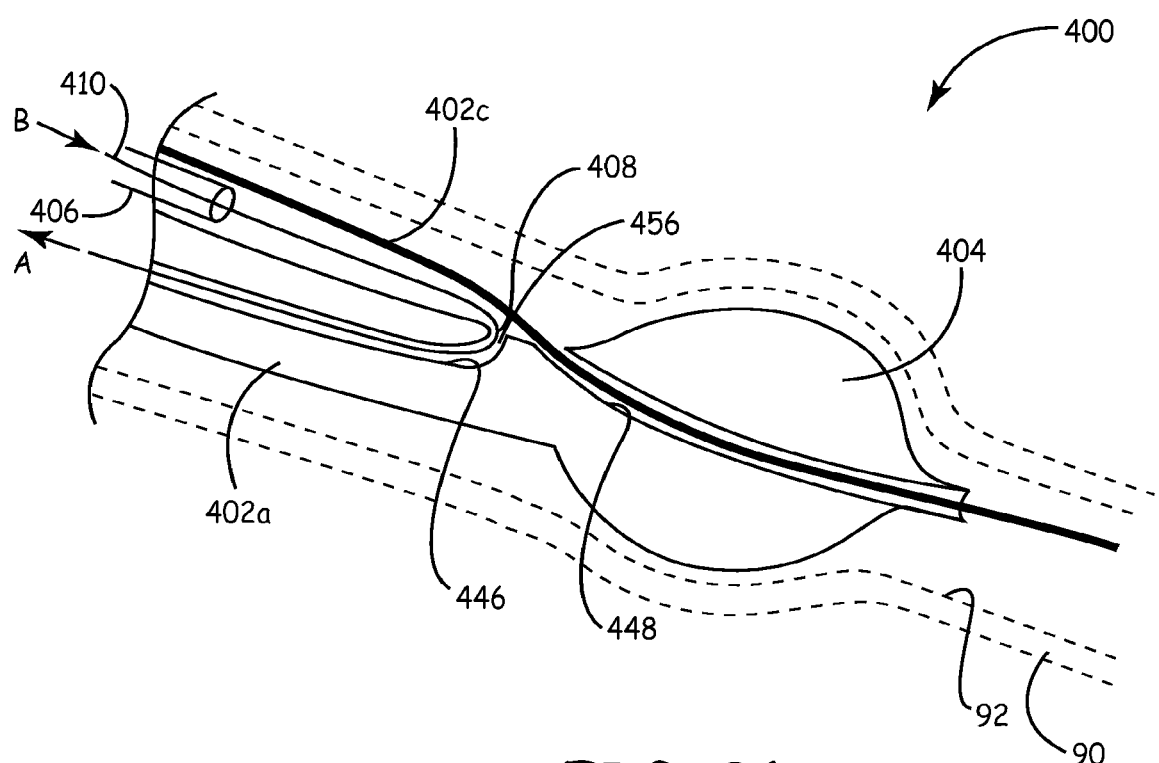
FIG. 31 is an environmental view of a lead delivery device according to various embodiments of the present teachings.
Figure 32:
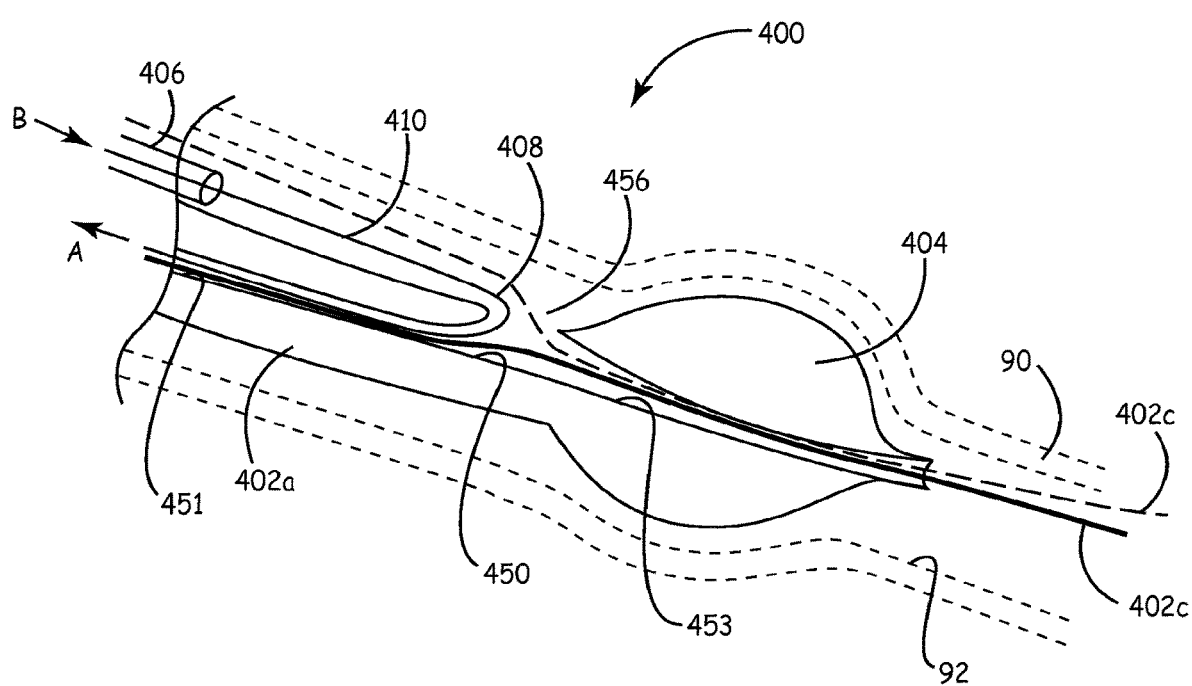
FIG. 32 is an environmental view of a lead delivery device according to various embodiments of the present teachings.

In various embodiments, the fixator 404 can be attached to a distal portion of the guidewire 402b or the catheter 402a as illustrated in various embodiments of FIGS. 30-32 (dimensions not in scale).

Referring to FIG. 30, for example, the guidewire 402b can include a fixator 404 attached to the distal portion 452 of the guidewire 402b for anchoring into the lumen 92 of a blood vessel 90. The guidewire 402b can include a guidewire lumen 442 with a side opening 454 that forms the pulley structure 408 The flexible member 410 can pass though the guidewire lumen 442, out of the side opening 454 and around the pulley structure 408 and extend between the guidewire 402b and the lumen 92 of the blood vessel 90. In various embodiments, the guidewire 402b can be pre-loaded with the flexible member 410. Once the guidewire 402b is positioned and fixated in the blood vessel 90, the lead 406 can be attached to the flexible member 410. Pulling the flexible member 410 in the direction A advances the lead 406 in the direction B.

Referring to FIG. 31, the fixator 404 can be attached to the catheter 402a. The catheter 402a can include a first lumen 446 with a side opening 456 that forms the pulley structure 408. The flexible member 410 can pass though the first lumen 446, out of the side opening 456 and around the pulley structure 408 and extend between the catheter 402a and the lumen 92 of the blood vessel 90. A relatively small diameter hollow or solid guidewire 402c can pass through a second lumen 448 through the fixator 404 for guiding the catheter 402a. Once the catheter 402a is positioned and fixated in the blood vessel 90, the lead 406 can be attached to the flexible member 410. Pulling the flexible member 410 in the direction A advances the lead 406 in the direction B.

Referring to FIG. 32, the fixator 404 can be attached to the catheter 402a. The catheter 402a can include a lumen 450 having a side opening 456 that forms the pulley structure 408. The lumen 450 can include a first or proximal lumen portion 451 and a second or distal lumen portion 453. The second lumen portion 453 can pass through the fixator 404. The flexible member 410 can pass though the first lumen portion 451, out of the side opening 456 and around the pulley structure 408 and can extend between the catheter 402a and the lumen 92 of the blood vessel 90. A small diameter hollow or solid cross-section guidewire 402c can extend through the first lumen portion 451 and the second lumen portion 453 for guiding the catheter 402a. The guidewire 402c can be first positioned in the blood vessel 90 and the catheter 402a pre-loaded with the flexible member can be positioned over the guidewire 402c. Pulling the flexible member 410 in the direction A advances the lead 406 in the direction B. Alternatively, the guidewire 402c can pass through the side opening 456 only though the second lumen portion 453, as shown in phantom line.

The various embodiments described above in connection with FIGS. 23-32 facilitate the implantation of a lead 406 using a pulley structure 408 and allow the physician to deliver the lead 406 to a target site by a pulling action rather than pushing. Because pulling a thin elongated member through a curved lumen can avoid buckling, kinking or other convolutions that may occur when pushing is used instead, a lead delivery device 400 using a pulley structure can utilize smaller diameters or reduced stiffness for the lead as well as the catheters and/or guidewires.

Referring to FIGS. 33-37C, a lead delivery device 500 and associated methods are illustrated according to various exemplary embodiments. The lead delivery device 500 is similar in certain respects to the lead delivery device 400 described above. Structural elements that are generally common or equivalent between the lead delivery devices 400 and 500 are denoted by numerals sharing the second and third digits. For example, the electrically conductive medical lead is referenced by the numeral 506 for the lead delivery device 500.

In various embodiments, the lead delivery device 500 can employ a push method for advancing the lead without using a pulley-like structure to advance the lead. In various embodiments, the lead delivery device 500 can employ a lead advancement member 562 that functions as a guiding rail or a pusher for pushing the medical lead over a delivery shaft to the target site, as discussed below in connection with FIGS. 33-37C. In various other embodiments, the lead delivery can include hydraulic pressure or vacuum suction with or without a pulley structure to advance the lead, as discussed below in connection with FIGS. 38A-42B.

Figure 33:
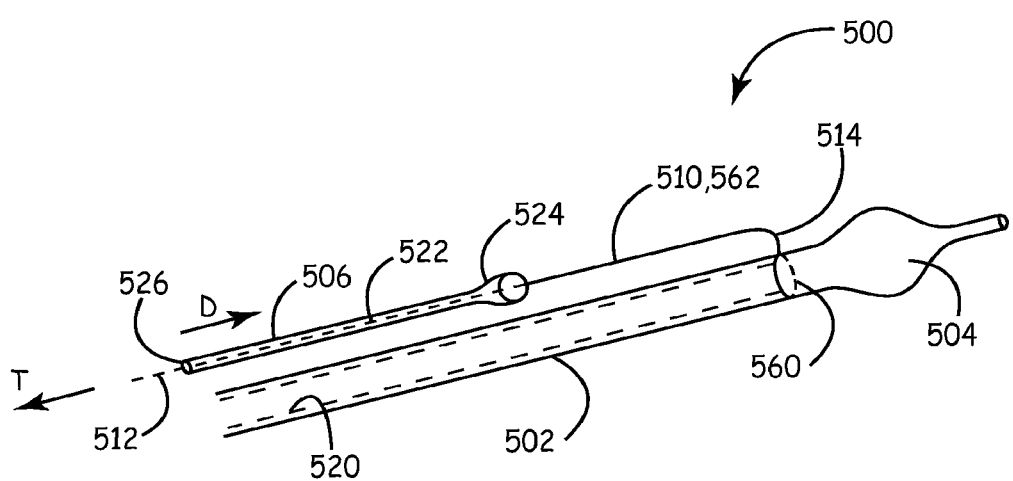
FIG. 33 is a perspective view of a lead delivery device according to various embodiments of the present teachings.

An exemplary embodiment of the lead delivery device 500 is illustrated in FIG. 33 largely diagrammatically. The lead delivery device 500 can include a delivery shaft 502, a fixator/fixation device 504 for temporary fixation during lead delivery and an electrically conductive medical lead 506 for an implantable medical device 290 (shown in FIG. 2). In various embodiments, the delivery shaft 502 can be an elongated member, such as, for example, a catheter or a guidewire either with or without an inner fixator lumen 520. The medical lead 506 can have either a solid body or a cannulated body with an internal lead lumen 522 and first and second ends 524, 526. The medical lead 506 can be coupled to the delivery shaft 502 with a lead advancement member 562 which can be in the form of a stiff wire or a substantially rigid guiding rail or a flexible member referenced as 510, such a string, thread or thin wire, or a combination thereof. The flexible member 510 can include first and second end portions 512, 514. In the embodiment of FIG. 33, the flexible member 510 can pass through the lead lumen 522 of the medical lead 506 and be attached at the second end portion 514 by an attachment device, such as, for example, by looping and tying the second end portion 514 around the delivery shaft 502 forming a connector 560, such as, for example, a loop or ring 560 around the delivery shaft 502. Once the delivery shaft 502 is anchored via the fixator 504 in the target cardiac site, the medical lead 506 can be pushed along and over the flexible member 510 in the direction of arrow D. The flexible member 510 can be kept taut by applying tension at the first (proximal) portion 512 in the direction of arrow T (opposite to the direction D). When a stiff guiding rail is used for the lead advancement member 562 in place of the flexible member 510, the medical lead 506 can be pushed over the lead advancement member 562 without tensioning. The fixator 504 can be detached, for example, by deflating or un-deploying the fixator 504. The delivery shaft 502 with the flexible member 510 can then be removed by pulling in the direction T away from the target site.

With further reference to FIG. 33, the lead advancement member 562 can be permanently or temporarily attached to the delivery shaft 502. The lead advancement member 562 can be flexible, similar to a floppy string, and able to easily attach to the delivery shaft 502. The lead advancement member 562 can have a connector 560 with a preformed shape on its distal portion 514 and may attach to the delivery shaft 502 without collapsing the inner lumen 520 of the delivery shaft 502. In other embodiments, the lead advancement member 562 can be attached to the delivery shaft 502 by crimping or by adhesive. A piece of heat shrink may also be placed over the lead advancement member 562 to secure it to the delivery shaft 502. A groove may be cut into the delivery shaft 502 to better place the lead advancement member onto the delivery shaft.

The lead advancement member is able to be loaded through or onto a medical lead by having a stiff portion, like a stylet wire, attached to its proximal end for threading through lead. This proximal portion of the lead advancement member may then be removed, by cutting for instance, after successfully loading the lead. The lead advancement member could be a stand alone product to be used or paired with any available common delivery shaft.

Figure 34A:
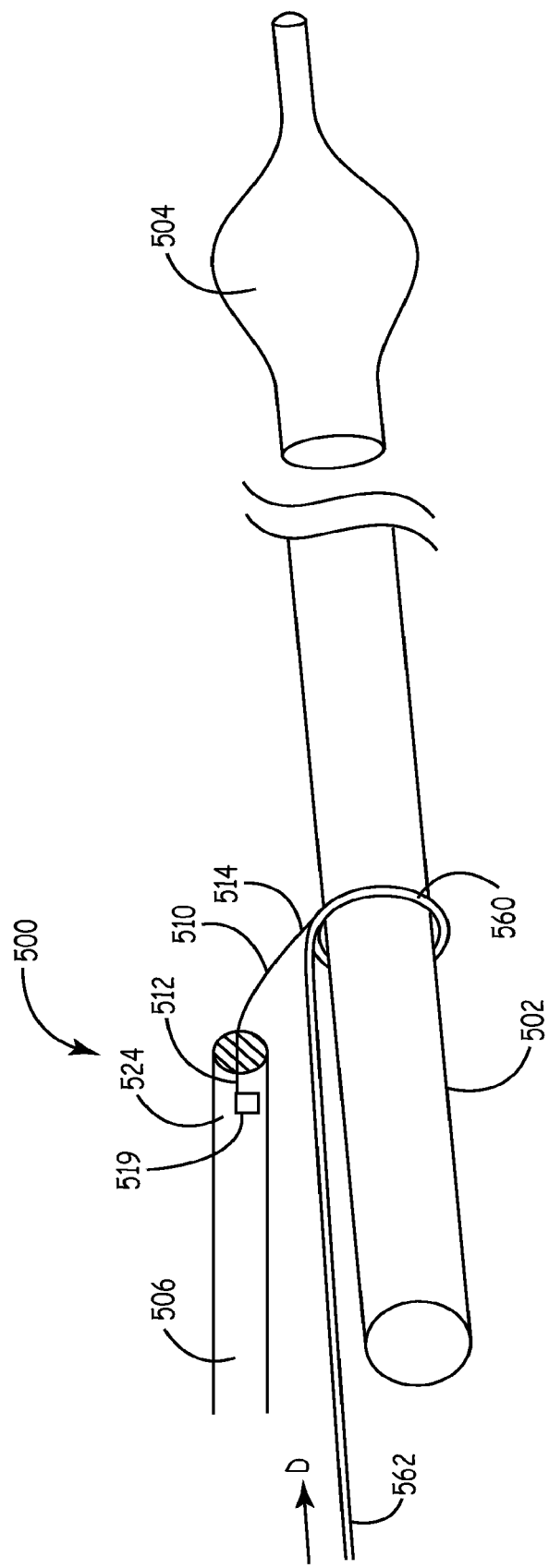
FIG. 34A is a perspective view of a lead delivery device according to various embodiments of the present teachings.
Figure 34B:
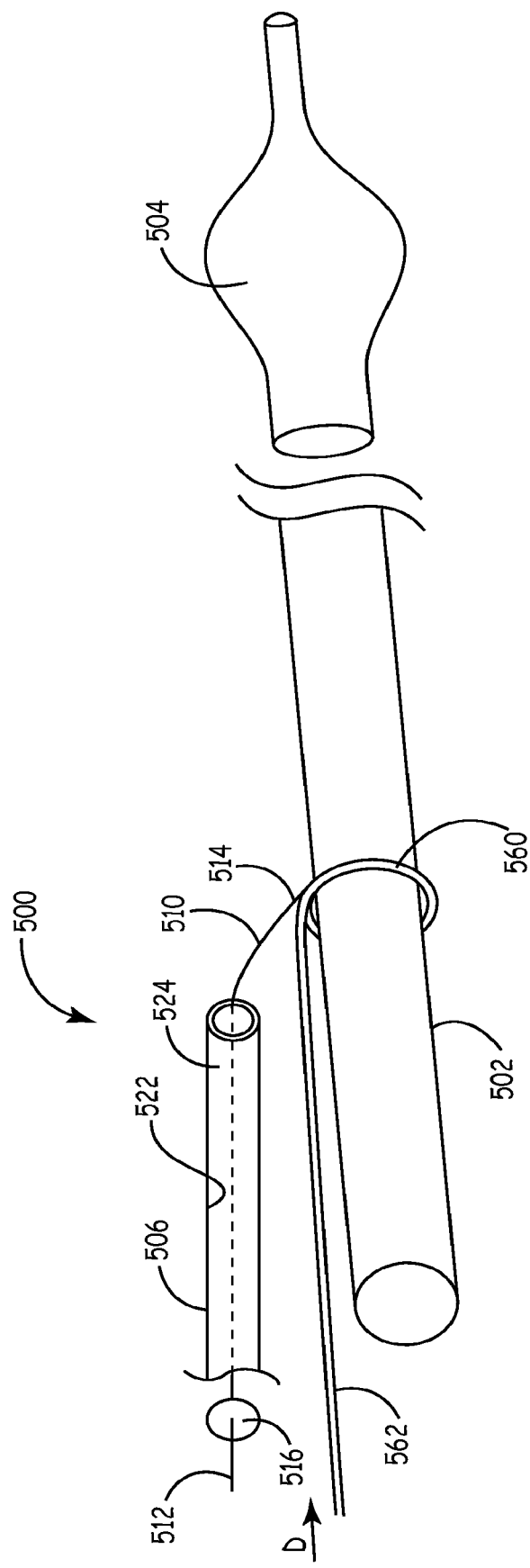
FIG. 34B is a perspective view of a lead delivery device according to various embodiments of the present teachings.
Figure 34C:
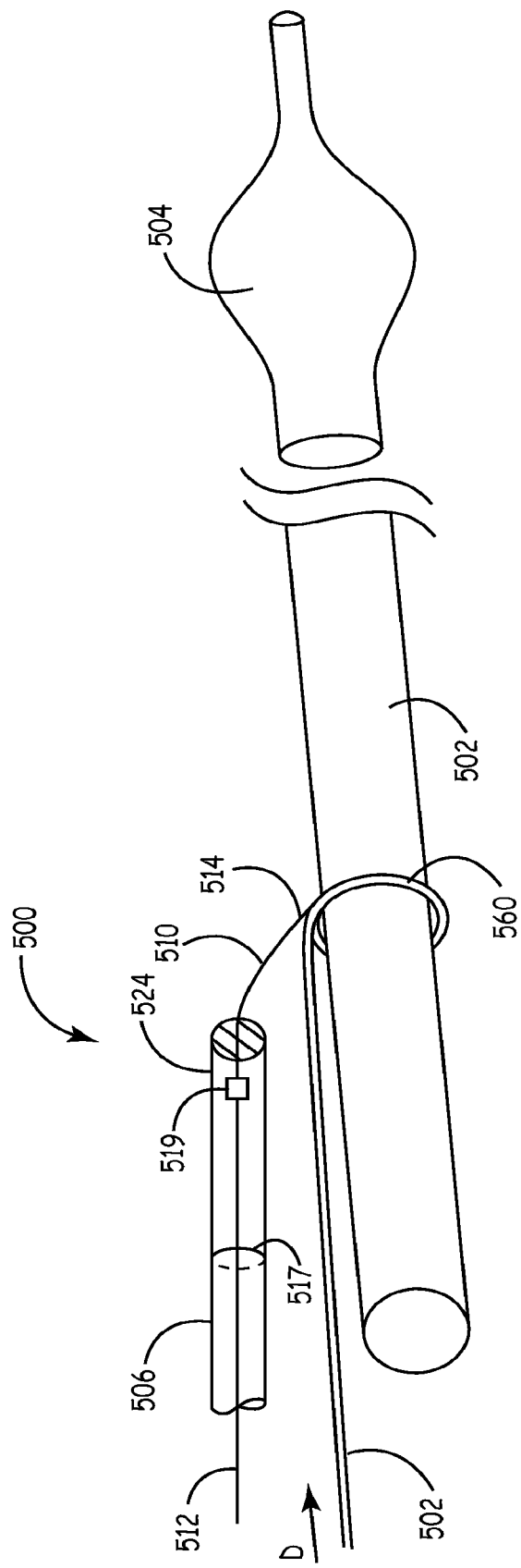
FIG. 34C is a perspective view of a lead delivery device according to various embodiments of the present teachings.

In various embodiments, and referring to FIGS. 34A-34C, a separate guiding rail or an elongated lead advancement member 562 can be used to push the medical lead 506 along the delivery shaft 502. The lead advancement member 562 can be a wire or other relative stiff or rigid member coupled to delivery shaft 502 with a connector, which can be an integral external eyelet or ring 560 which is slidably disposed around the delivery shaft 502. The lead advancement member 562 can be pushed in the direction of arrow D, pushing the connector or ring 560 and the medical lead 506 toward the target site along the same direction D. In various embodiments, the medical lead 506 can be coupled to the lead advancement member 562 or the ring 560 by a flexible member 510 that extends between a retainer 519 adjacent to the distal end 524 of the medical lead 506 and the ring 560 or a portion of the lead advancement member 562 adjacent to the ring 560, as illustrated in FIG. 34A. The retainer 519 can be any of the types of retainer described above and similar to the retainer 419 of the lead delivery device 400 illustrated in FIG. 23A. In other embodiments, and as illustrated in FIG. 34B, the flexible member 510 can pass through the lead lumen 522 and can be coupled to the medical lead 506 by a retainer 516, similar to the retainer 416 discussed above in connection with FIG. 23. In other embodiments, and as illustrated in FIG. 34C, the flexible member 510 can remain outside the medical lead 506 and can be coupled loosely to the medical lead 506 by retainers 517 or 519, similar to the retainers 417 and 419 discussed above in connection with FIG. 23A. Additional means of removably connecting the medical lead 506 to the delivery shaft 502 or the flexible member 510 are illustrated in FIGS. 43-53 and are described below.

Figure 35A:
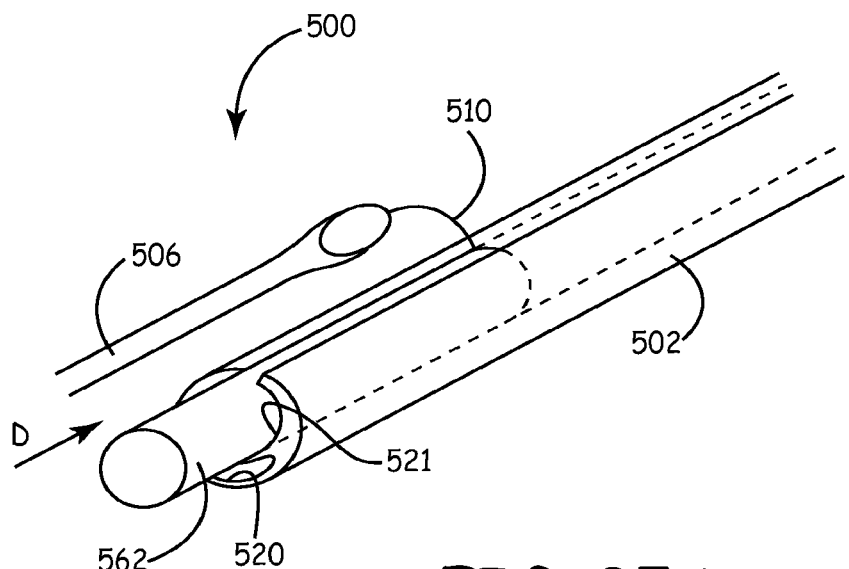
FIG. 35A is a perspective view of a lead delivery device according to various embodiments of the present teachings.
Figure 35B:
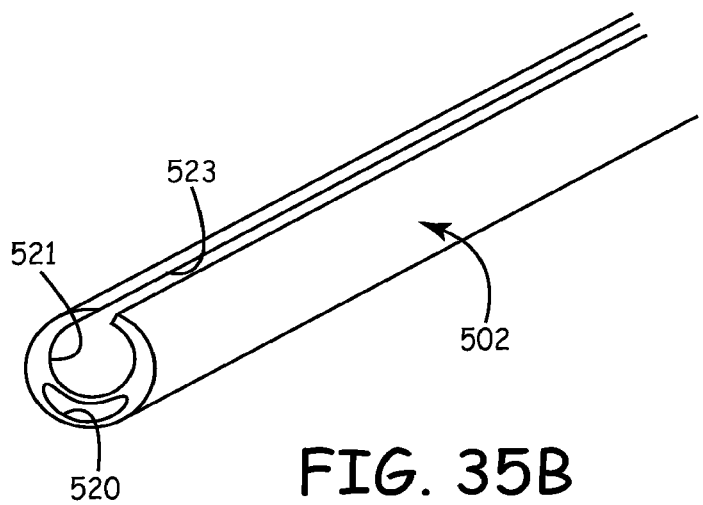
FIG. 35B is a perspective view of a delivery shaft of the lead delivery device of FIG. 35A.

In various embodiments, and referring to FIGS. 35A and 35B, the lead delivery device 500 can include an elongated lead advancement member 562 that is slidably received in a delivery lumen 521 of the delivery shaft 502. The delivery lumen 521 can be open to the outer surface of the delivery shaft 502 forming an open channel that communicates with an external longitudinal slot 523 for connection with the medical lead 506 via the flexible member 510. The open delivery lumen 521 can be a separate lumen and non-communicating with a fixator lumen 520 which is used for deploying the fixator 504, such as for inflating a balloon-like fixator 504, for example. The medical lead 506 can be advanced in the direction of the arrow D by pushing the lead advancement member 562 along the delivery lumen 521 in the same direction D.

Figure 36:
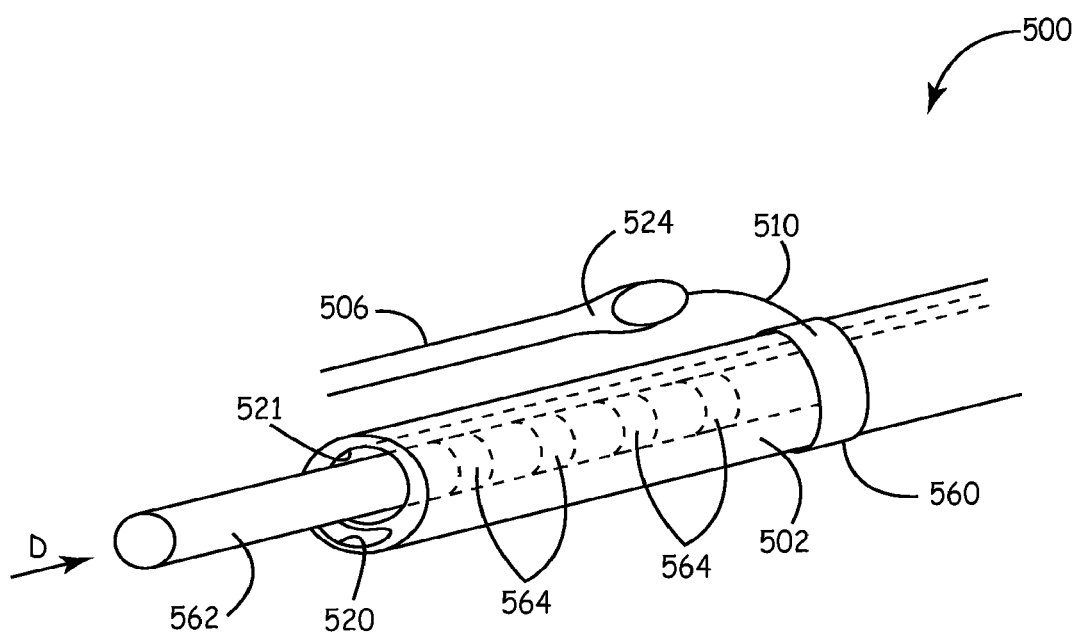
FIG. 36 is a perspective view of a lead delivery device according to various embodiments of the present teachings.

Referring to FIG. 36, the lead advancement member 562 can include a distal magnetized/magnetic portion 564 that can interact magnetically with a magnetized/magnetic eyelet or ring 560. The ring 560 can be coupled to the distal end 524 of the medical lead 506 via a flexible member 510. The ring 560 can be slidably disposed externally around the delivery shaft 502. Magnetic interaction can advance the medical lead 506 in the direction D, while the lead advancement member 562 is pushed in the direction D inside a closed delivery lumen 521 of the delivery shaft 502. The magnetic portion 564 and the magnetic ring 560 can interact by repulsive magnetic forces (similar magnetic polarity) such that the ring 560 moves ahead of the magnetic portion 564 as the delivery shaft 502 advances in the direction D. Alternatively, the magnetic portion 564 and the magnetic ring 560 can interact by attractive magnetic forces (opposite magnetic polarity), such that the ring 560 moves together with the magnetic portion 564 as the delivery shaft advances in the direction D.

Figure 37A:
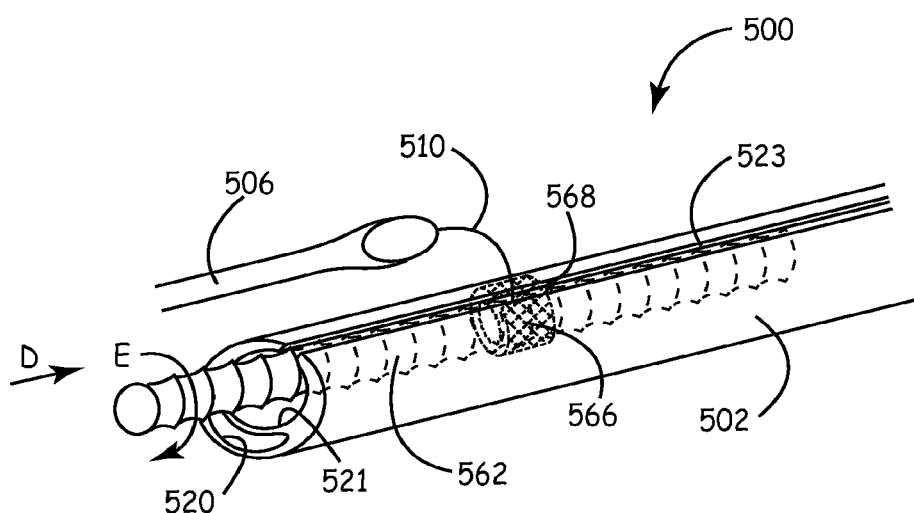
FIG. 37A is a perspective view of a lead delivery device according to various embodiments of the present teachings.
Figure 37B:
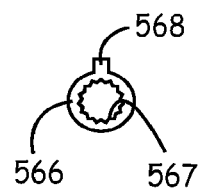
FIG. 37B is a cross-sectional view of a threaded nut of the lead delivery device of the lead delivery device of FIG. 37A.
Figure 37C:
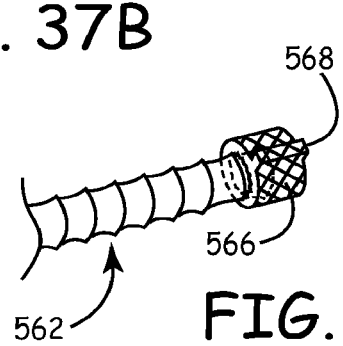
FIG. 37C is a perspective view of a threaded member of the lead delivery device of FIG. 37A.

Referring to FIGS. 37A, 37B and 37C, the lead advancement member 562 can be in the form of a threaded elongated member, which is threadably connected to an inner threaded lumen 567 of a nut 566. The nut 566 can include an anti rotation feature, such as tab 568 that extends outside the open delivery lumen 521 through an external slot 523. Rotating the advancement member 562 in the direction of the curved arrow E causes the nut 566 to slide along the delivery shaft 502 in the direction of arrow D. The medical lead 506 can be coupled to the nut 566 and move along the delivery shaft 502 together with the nut 566. The medical lead 506 can be coupled to the nut 566 with any of the various connections discussed above. For example, the medical lead 506 can be connected to the tab 568 with a flexible member 510 directly connected to the tab 568. The flexible member 510 can be indirectly connected to the tab 568 by magnetic forces between a magnetized portion of the tab 568 and a magnetized portion of an external ring 560 around the delivery shaft 502, with the ring 560 coupled to the flexible member 510, as described in connection with FIG. 36.

Figure 38A:
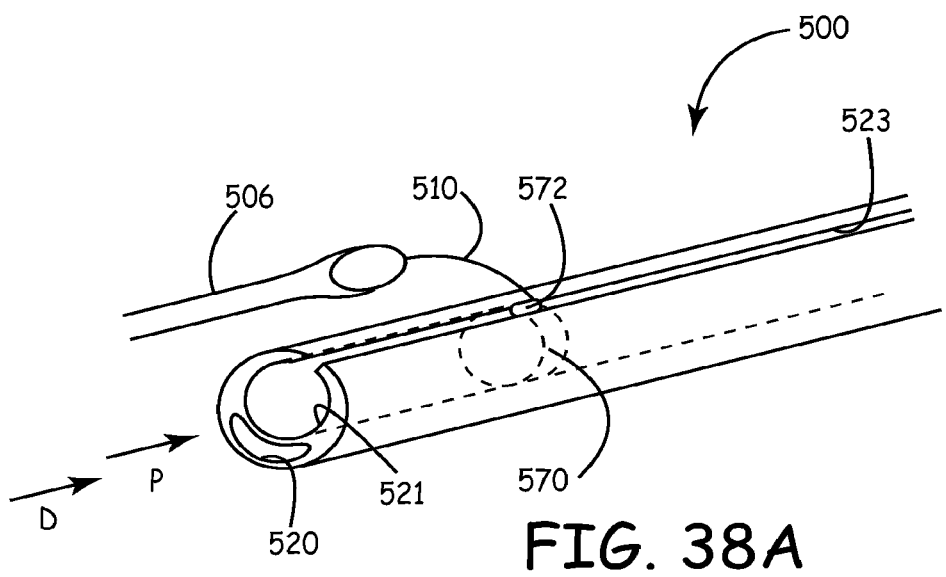
FIG. 38A is a perspective view of a lead delivery device according to various embodiments of the present teachings.
Figure 38B:
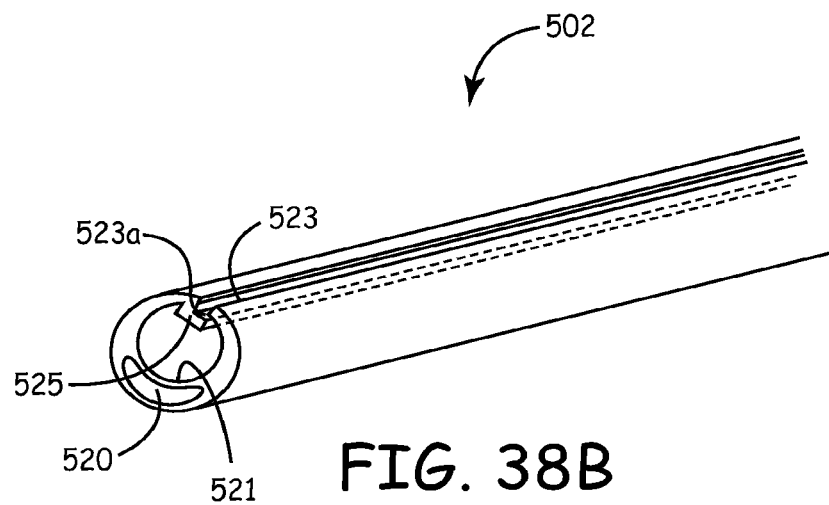
FIG. 38B is a perspective view of a shaft of the lead delivery device of FIG. 38A.
Figure 39:
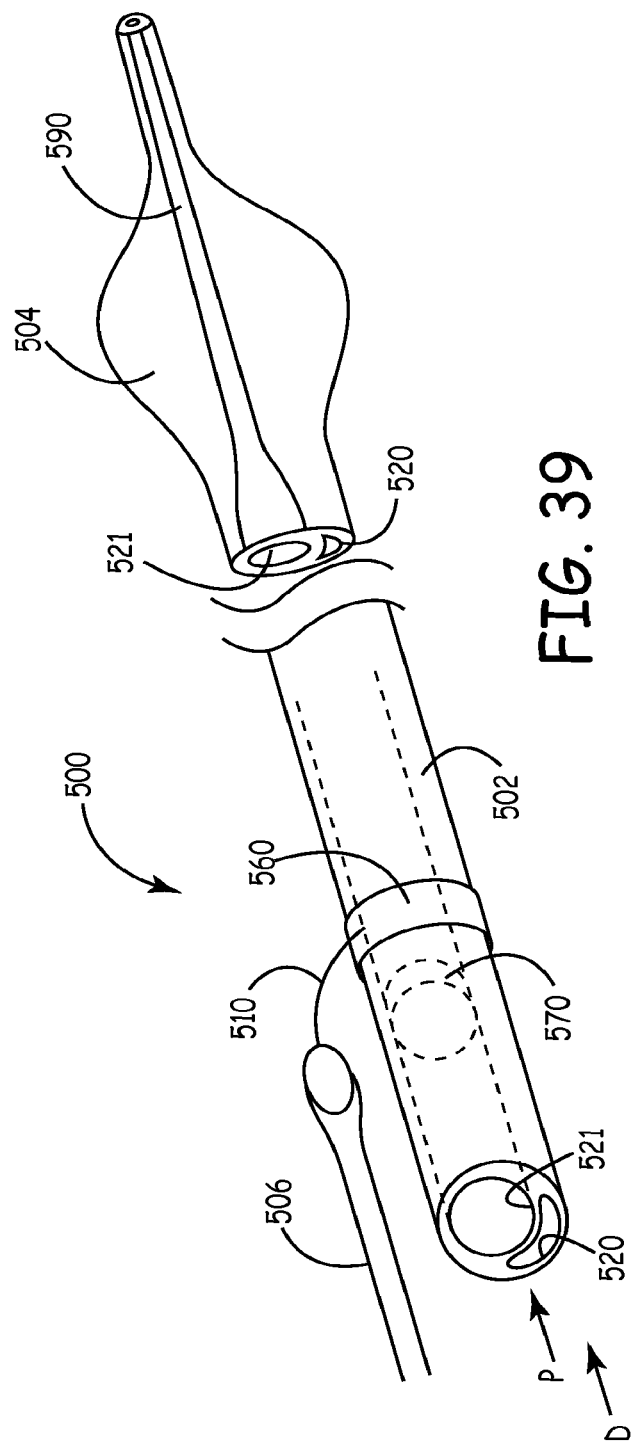
FIG. 39 is a perspective view of a lead delivery device according to various embodiments of the present teachings.

Referring to FIGS. 38A-39, the lead advancement member can be in the form of hydraulic pressure p exerted on a hydraulic plug 570 coupled to the medical lead 506. In FIG. 38A, for example, the flexible member 510 is coupled to and extends between the medical lead 506 and a tab 572 that extends from the hydraulic plug 570 and protrudes through the longitudinal slot 523 of the delivery lumen 521 of the delivery shaft 502. Hydraulic pressure p can be provided through the flow of a liquid medium, including blood or a saline solution. The delivery lumen 521 and the longitudinal slot 523 can include a sealing structure 525 for reducing leakage of the liquid. For example, the delivery shaft 502 can include a sealing structure 525 in the form of an extension under the slot 523, such that communication between the longitudinal slot 523 and the delivery lumen 521 is redirected to a small opening 523a under and at an offset from the opening of the longitudinal slot 523, as shown in FIG. 38B. In other embodiments, the sealing structure 525 can be a flexible flap or hydraulic valve or other sealing member that opens sufficiently to allow the passage of the tab 572 to pass and closes behind the tab 572 to reduce leakage through the longitudinal slot 523 of the delivery shaft 502. Under the effect of the hydraulic pressure, the hydraulic plug 570 and the medical lead 506 move in the direction of arrow D toward the target site.

In other embodiments, as illustrated for example in FIG. 39, the delivery lumen 521 can have a closed-channel cross-section. Magnetic coupling can be used between the hydraulic plug 570 and an external ring 560 slidably surrounding the delivery shaft 502 and coupled to the medical lead 506 via a flexible member 510, as also described in connection with FIG. 36. Under the effect of the hydraulic pressure p, the hydraulic plug 570 and the medical lead 506 can move in the direction of arrow D toward the target site.

Venting can be provided by a vent 590 that passes through the fixator 504 or through other location proximal to the fixator 504.

Figure 40:
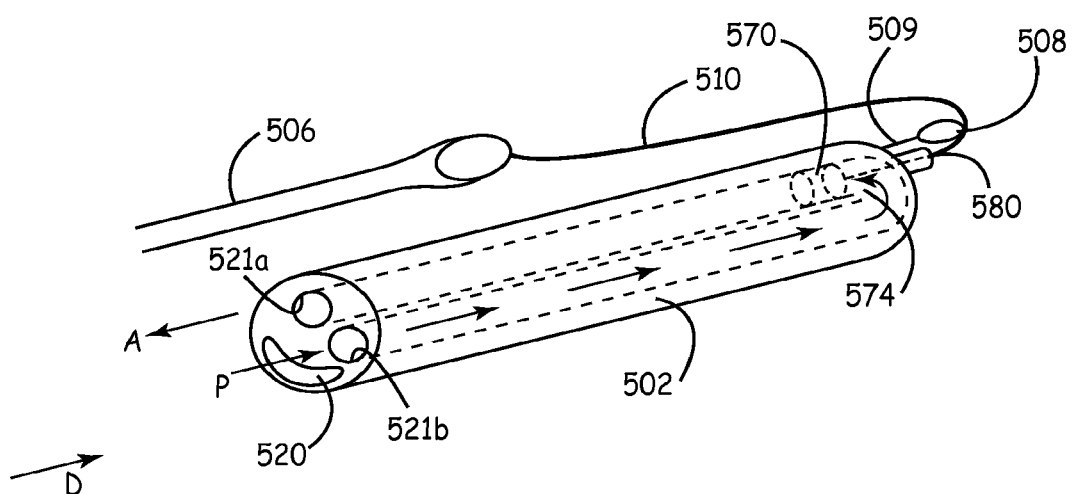
FIG. 40 is a perspective view of a lead delivery device according to various embodiments of the present teachings.

In various embodiments, as illustrated for example in FIG. 40, hydraulic pressure p can be used with a pulley structure 508 to advance the medical lead 506 in the direction of arrow D toward the target site (away from the physician). The pulley structure 508 can be attached to the delivery shaft 502 with a support element 509, such as a rod. The delivery shaft 502 can include first and second delivery lumens 521a and 521b. The first and second delivery lumens 521a and 521b can be separate lumens that communicate at a U-shaped junction 574 at their distal ends. Hydraulic pressure p can be applied through the second delivery lumen 521b in the direction of arrow D. The hydraulic liquid passes through the U-shape junction 574 and exerts pressure on the hydraulic plug 570 in the direction A, opposite to the direction D, along the first delivery lumen 521a. The hydraulic plug 570 can be coupled to the medical lead 506 via a flexible member 510 which changes direction making a U-turn as the flexible member 510 passes by a pulley structure 508, similar to the pulley structures 408 described above in connection with the lead delivery system 400. The flexible member 510 can be coupled to the hydraulic plug 570 through a gasket, a valve or other sealing member 580 to minimize leakage at the entry into the first delivery lumen 521a. As the hydraulic pressure p pushes the hydraulic plug 570 in the direction A, the medical lead advances in the direction D toward the target site (away from the physician).

Figure 41:
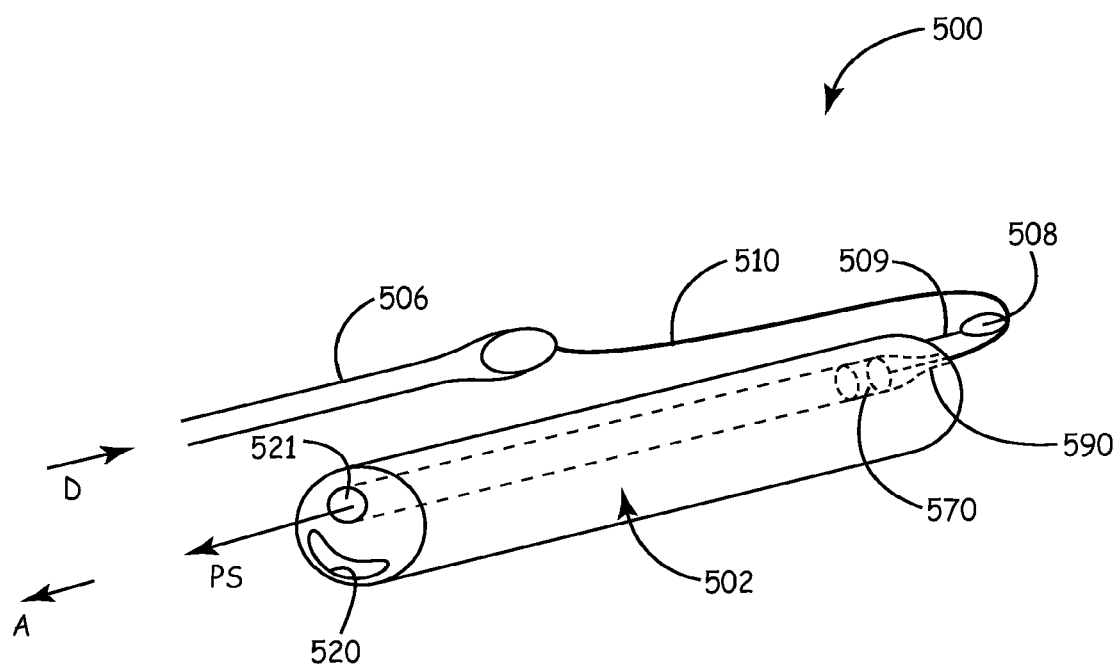
FIG. 41 is a perspective view of a lead delivery device according to various embodiments of the present teachings.

Hydraulic vacuum suction (negative pressure) "ps" can be used with a pulley structure 508 to advance the medical lead in the direction of arrow D toward the target site (away from the physician), as illustrated in FIG. 41. The medical lead 506 can be coupled to a flexible member 510, which passes by a pulley structure 508 and is coupled to the hydraulic plug 570 through an opening or vent 590. When suction ps is applied in the direction A, which is opposite to the direction D, the hydraulic plug 570 can move in the direction A, while the medical lead 506 moves in the direction D. Leakage during lead delivery can be avoided by using suction.

Referring to FIGS. 42A and 42B, hydraulic pressure p can be applied directly to the medical lead 506 to advance the medical lead 506 in the direction D toward the target site. The medical lead 506 can be inserted in the delivery lumen 521 and pressure p can be applied through the delivery lumen 521 against an enlarged head portion 506a of the medical lead 506, as shown in FIG. 42A. To limit leakage of the hydraulic fluid, pressure p can be applied through a side port or side opening 584 of the delivery shaft 502. A gasket or a valve or other sealing member 580 with flexible flaps 582 can be used proximally to the side opening 584 to limit leakage around the medical lead 506 at the proximal end of the delivery shaft 502. Venting can be provided by a vent 590 that passes through the fixator 504 or through other location proximal to the fixator 504.

Referring to FIGS. 43-53, various exemplary means for removably connecting the medical lead 506 to the delivery shaft 502 or to a flexible member are illustrated. The lead attachment/detachment means illustrated in these figures can be used interchangeably in any of the embodiments described above such that the medical lead 506 can be removably connected to the delivery shaft 502 or to the flexible member 510.

Figure 43:
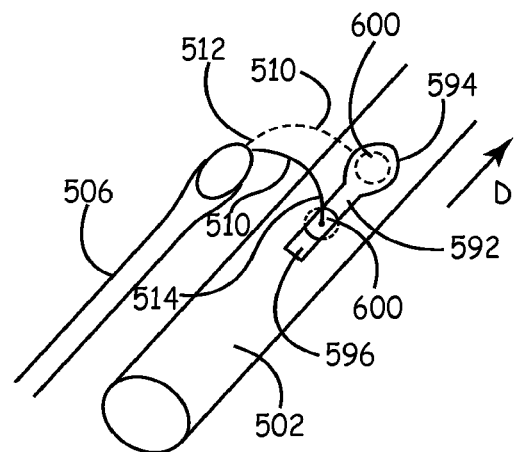
FIGS. 43-47B are perspective views illustrating various means of removably connecting a medical lead to a delivery shaft according to the present teachings.

Referring to FIG. 43, the medical lead 506 can be connected to the delivery shaft 502 using a removable connection similar to chain lock on a door. The delivery shaft can include a keyhole-shaped slot 592 including a longitudinal slot 596 and an enlarged opening 594 that is wider than the longitudinal slot 596. The first end 512 of the flexible member 510 is attached to the medical lead 506 and the second end 514 to a pin or disk 600 which can be inserted in and removed from the slot 592 through the enlarged opening 594, as shown in FIG. 43. The position of the flexible member 510 with the disk 600 during attachment or removal from the slot 592 of the delivery shaft 502 is shown in phantom line. In exemplary illustration of FIG. 43, the medical lead 506 is moved by pushing the delivery shaft 502 in the direction D.

Figure 44:
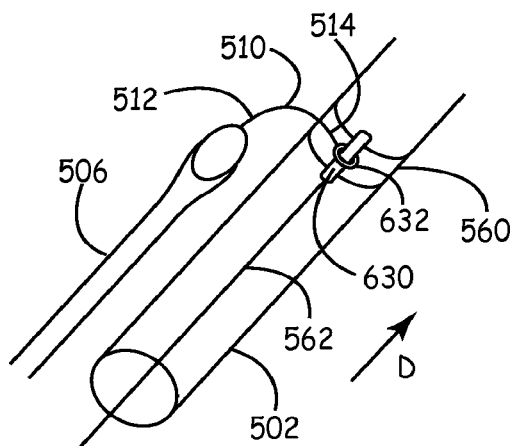

Referring to FIG. 44, the lead advancement member 562 includes a pin 630, which is attached to the ring 560 at an intermediate pin portion between the ends of the pin 630. The ring 560 can slide over the delivery shaft 502, as described above. The first end 512 of the flexible member 510 is attached to the medical lead 506 and the second end includes a loop 632 that slides over the pin 630. The loop 632 is held by the pin 630 when the lead advancement member 562 is pushed toward the target site in the direction D, and slides off the end of the pin 630, when the lead advancement member 562 is retracted in the opposite direction away from the target site.

Figure 45:
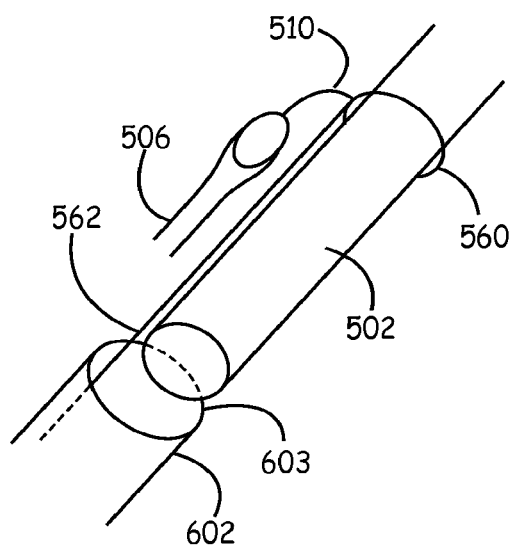

Referring to FIG. 45, an outer catheter 602 having a sharp distal tip 603 can be slid over the lead advancement member 562 and the delivery shaft 502 to cut the flexible member 510 after the medical lead 506 has reached the target site.

Figure 46:
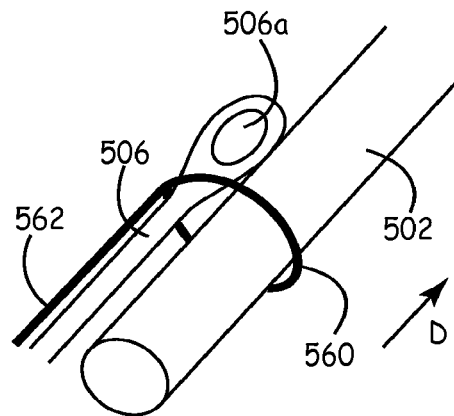
Figure 47A:
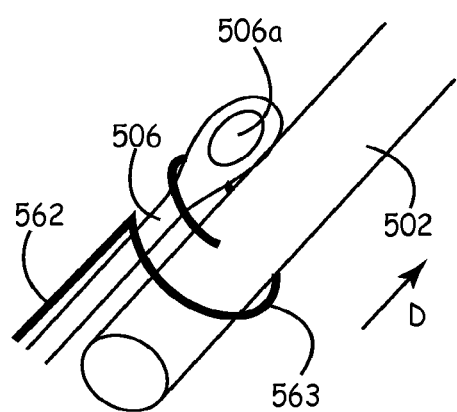
Figure 47B:
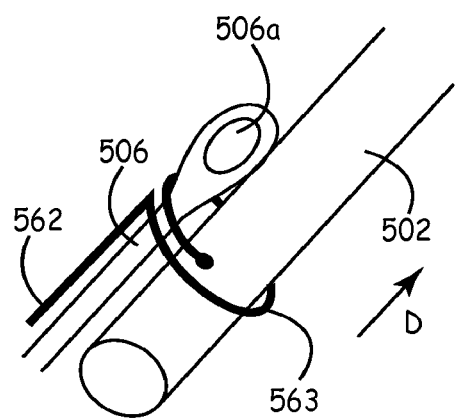

Referring to FIG. 46, the ring 560 on the lead advancement member is sized so that the ring 560 can push against the head 506a of the medical lead 506 to push the medical lead 506 along the delivery shaft 502 toward the target site. Once the medical lead 506 is delivered to the target site, the lead advancement member 562 can be pulled off the medical lead 506 in the opposite direction. The connections illustrated in FIGS. 47A and 47B operate similarly, except that the ring can be in the form of a corkscrew-like ring 563. The corkscrew-like shape can facilitate loading the delivery shaft 502 and the medical lead 506 into the lead advancement member 562. The lead advancement member 562 can be removed either by pulling back in the direction opposite to the direction of delivery, direction D or by a rotating or unscrew-type of motion. The corkscrew ring 563 illustrated in FIG. 47B can be sized to be wrapped around the delivery shaft 502 more tightly, and have a tighter pitch, such that slight flexing of the corkscrew ring may be required for loading/unloading the medical lead 506 through the corkscrew-like ring 563. The corkscrew-like ring can be made of flexible elastically deformable material or shape-memory material, such as stainless steel wire, plastic material or nitinol, for example.

Figure 48A:
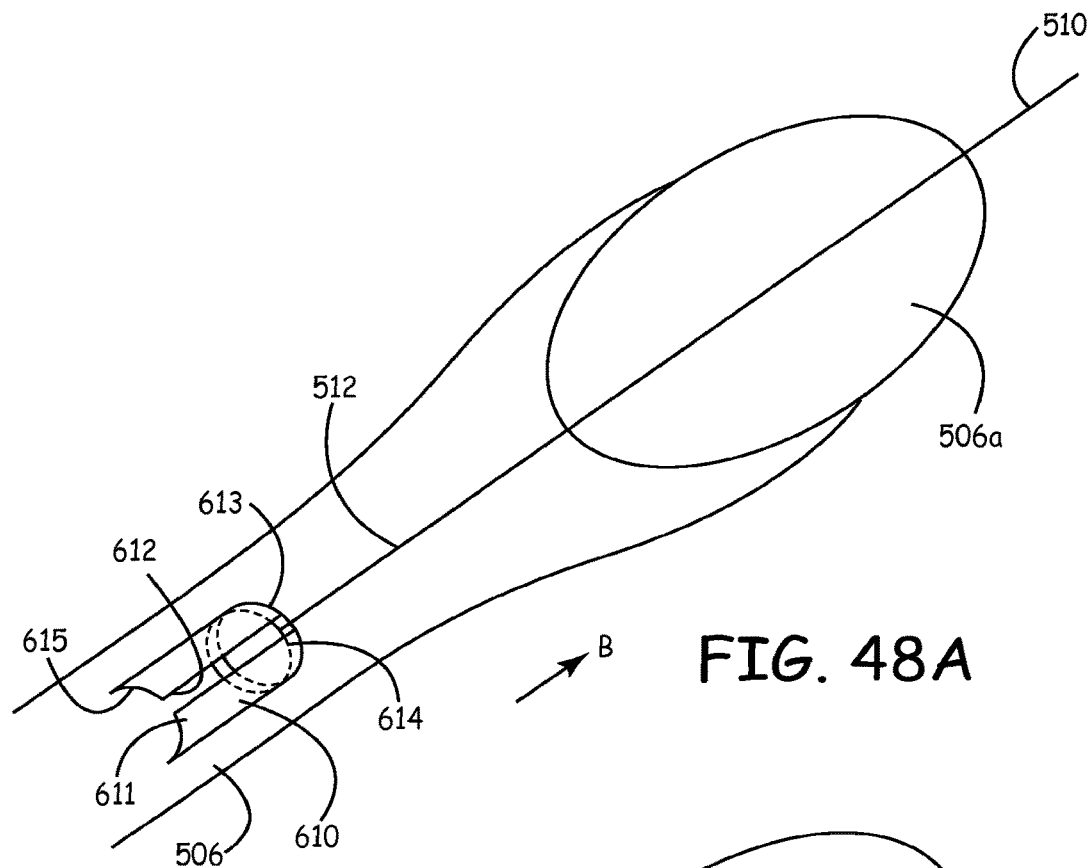
FIGS. 48A and 48B are perspective views illustrating means of removably connecting a medical lead to a flexible member according to the present teachings.
Figure 48B:
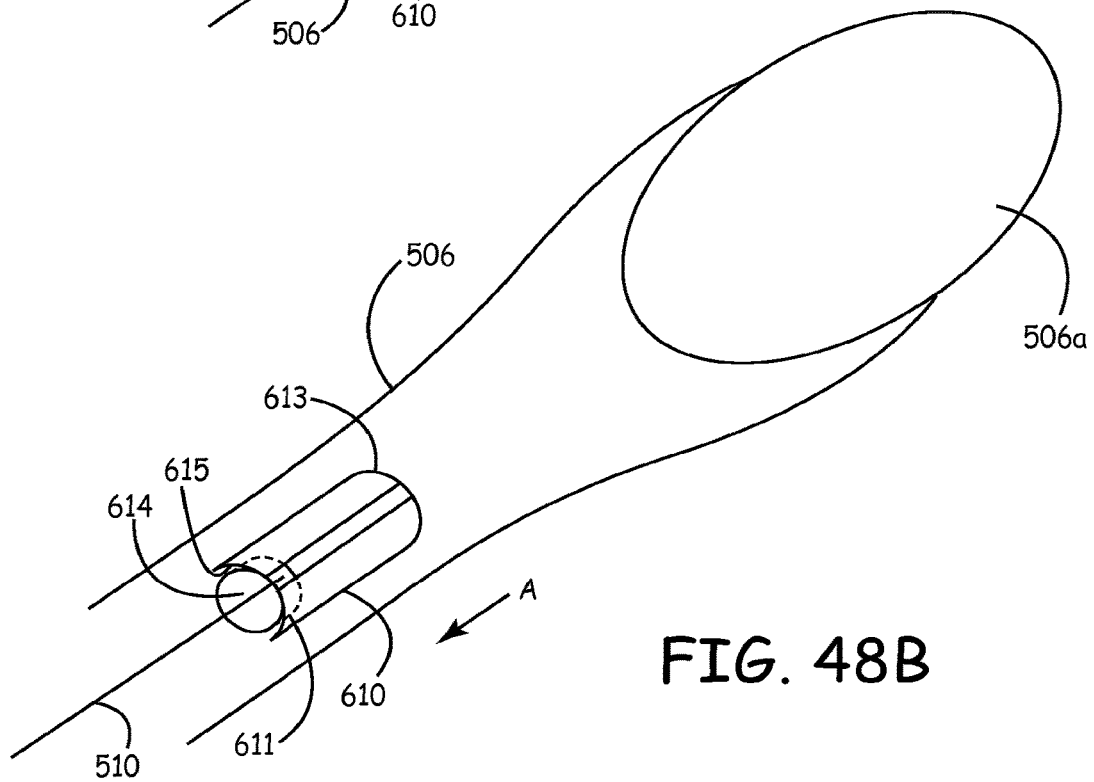

Referring to FIGS. 48A and 48B, a connection similar to the connection of FIG. 43 discussed above can used between the medical lead 506 and the flexible member 510. The medical lead 506 can include an external pocket 610 attached on an outer surface of the medical lead 506 adjacent to the head 506a. The pocket 610 defines an interior receptacle 615 with proximal open end 611 and a closed distal end 613. The pocket 610 includes a longitudinal narrow slot 612 that communicates with the interior receptacle 615. The proximal end 512 of the flexible member 510 can be attached to a pin or disk 614 which is received in the interior receptacle 615 with the proximal end 512 of the flexible member 510 extending through the slot 612 outside the pocket 610. Pulling the flexible member 510 in the direction of arrow B moves the medical lead 506 in the same direction B for delivery to the target sites, as shown in FIG. 48A. Pulling the flexible member 510 in the direction of arrow A moves the disk 614 out of the interior receptacle 615 of the pocket 610 and releases the flexible member 510. It is appreciated that the flexible member 510 can be attached to the lead advancement member 562 or the delivery shaft 502 in the manner described in any of the embodiments discussed above, in which the distal end of the flexible member 510 is coupled to the lead advancement member 562 or to the delivery shaft 502.

Figure 49:
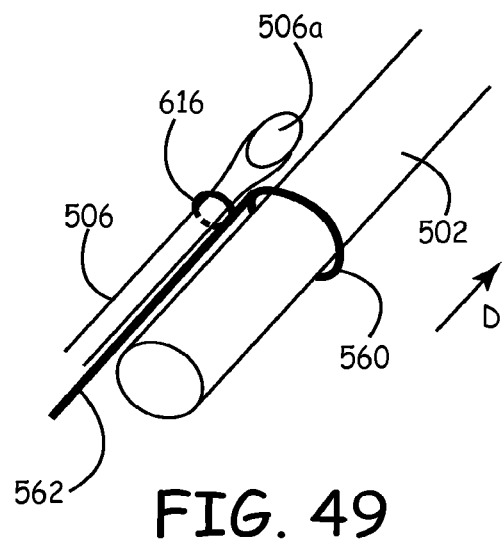
FIGS. 49-53 are perspective views illustrating various means of removably connecting a medical lead to a delivery shaft according to the present teachings.

Referring to FIG. 49, the medical lead 506 can be attached to the lead advancement member 562 with a flexible clip 616. After the medical lead 506 has been delivered to the target site, the clip 616 can be removed by pushing the lead advancement member 562 forward in the direction D, while holding the medical lead 506 stationary, such that the clip 616 is pulled over and off the head 506a of the medical lead 506.

Figure 50:
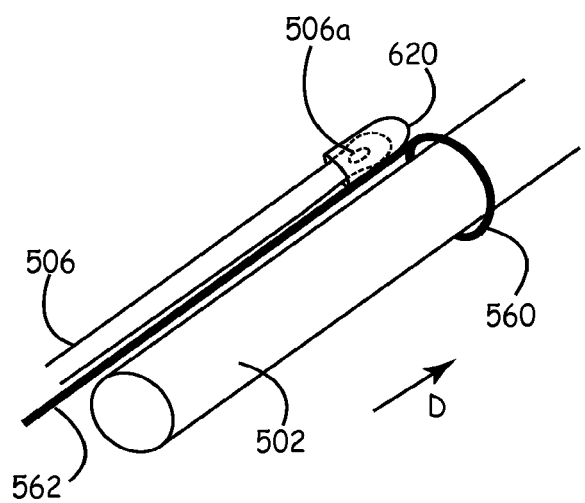

Referring to FIG. 50, the head 506a of the medical lead 506 can be placed into an elastic cap or other elastic enclosure 620 that is attached to the lead advancement member 562. After the medical lead 506 has been delivered to the target site, the elastic enclosure 620 can be removed by pushing the lead advancement member 562 forward in the direction D, while holding the medical lead 506 stationary, such that the elastic enclosure 620 is pulled off the head 506a of the medical lead 506.

Figure 51:
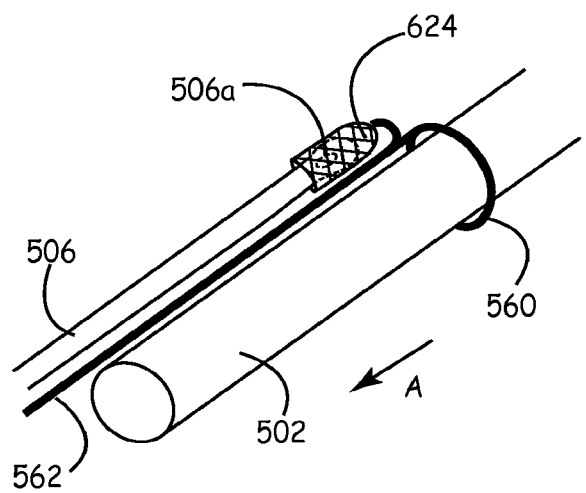

Referring to FIG. 51, the head 506a of the medical lead 506 can be placed into a braided mesh or braided and open ended enclosure 622 that is attached to the lead advancement member 562. The braided enclosure 622 can take a shape with a narrower diameter when in tension and a loose-fitting shape of larger diameter under compression. When the medical is being delivered to the target site, the braided enclosure 624 s in tension and holds the head 506a of the medical lead 506. After the medical lead 506 has been delivered to the target site, the braided enclosure 624 an be removed by holding the medical lead 506 stationary and pulling the lead advancement member 562 in the direction A to axially compress the braided enclosure 624 such the medical lead 506 can be pulled free and out of the loosened braided enclosure 624.

Figure 52:
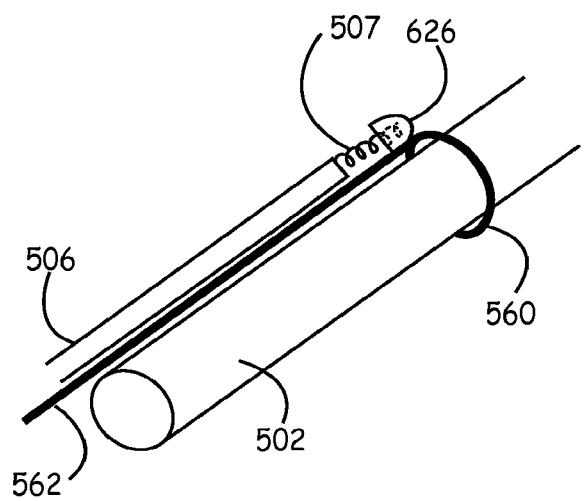

Referring to FIG. 52, the medical lead 506 can includes a distal active fixator in the form of a screw or helix 507. For delivery to the target site, the helix 507 can be removably screwed into a receptacle 626 which is attached to the lead advancement member 562. After the medical lead 506 has been delivered to the target site, the helix 507 can be unscrewed from the lead advancement member 562, which is then removed. The helix 507 can be screwed to cardiac tissue for active fixation of the medical lead 506.

Figure 53:
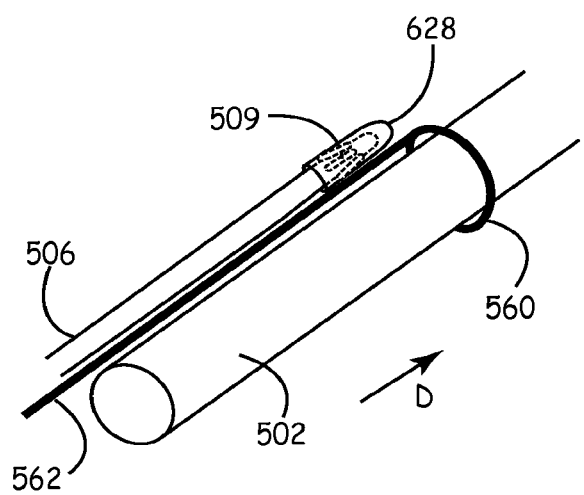

Referring to FIG. 53, the medical lead 506 can include a distal passive fixator in the form of compressible/expandable tines 509. For delivery to the target site, the tines 509 can be compressed into a receptacle 628 which is attached to the lead advancement member 562. After the medical lead 506 has been delivered to the target site, the receptacle 628 can be removed by pushing the lead advancement member 562 forward in the direction D, while holding the medical lead 506 stationary, such that the receptacle 628 is pulled off the medical lead 506 and the tines 509 expand for passive fixation.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A method of delivering a medical lead to an anatomic target site, the method comprising:
   providing an elongated delivery shaft comprising a distal end insertable to an anatomic target site of a patient, wherein the elongated delivery shaft defines a delivery lumen;
   providing an elongated lead advancement member extending between a proximal first end portion and a distal second end portion, wherein the elongated lead advancement member is received in the delivery lumen, and wherein the elongated lead advancement member comprises:
      a movement member configured to be moved along the elongated delivery shaft; and
      a connector movably coupled to the elongated delivery shaft and movable along the elongated delivery shaft towards the distal end thereof as the movement member is moved along the elongated delivery shaft; and
   providing a receptacle comprising an open end configured to receive a distal end of a lead and removably attach the distal end of the lead within the receptacle, wherein the receptacle is coupled to the elongated lead advancement member such that the receptacle is movable along the elongated delivery shaft as the movement member is moved along the elongated delivery shaft;
   inserting the elongated delivery shaft comprising the distal end to the anatomic target site;
   inserting the distal end of the lead into the receptacle to removably attach the distal end of the lead within the receptacle;
   slidably coupling the connector of the elongated lead advancement member to the delivery shaft;
   moving the elongated lead advancement member along the delivery shaft toward the anatomic target site using the movement member, thereby advancing the distal end of the lead removably attached within the receptacle toward the anatomic target site; and
   removing the distal end of the lead from within the receptacle.

2. The method of claim 1, wherein the receptacle comprises an elastic enclosure configured to receive the distal end of the lead and removably attach the distal end of the lead within the receptacle.

3. The method of claim 2, wherein the receptacle comprises an elastic cap configured to receive the distal end of the lead and removably attach the distal end of the lead within the receptacle.

4. The method of claim 2, wherein moving the elongated lead advancement member along the delivery shaft toward the anatomic target site comprises pushing the movement member along and toward the distal end of the elongated delivery shaft to move the distal end of the lead removably coupled within the elastic enclosure along the elongated delivery shaft.

5. The method of claim 4, wherein removing the distal end of the lead from within the receptacle comprises:
   holding the lead in a stationary position; and
   moving the movement member distally along the elongated delivery shaft to remove the receptacle from the distal end of the lead.

6. The method of claim 1, wherein inserting the distal end of the lead into the receptacle to removably attach the distal end of the lead within the receptacle comprises removably screwing a fixator at the distal end of the lead into the receptacle.

7. The method of claim 6, wherein moving the elongated lead advancement member along the delivery shaft toward the anatomic target site comprises pushing the movement member along and toward the distal end of the elongated delivery shaft to move the distal end of the lead removably screwed within the receptacle along the elongated delivery shaft with the movement member.

8. The method of claim 6, wherein removing the distal end of the lead from within the receptacle comprises unscrewing the fixator at the distal end of the lead from within the receptacle.

9. The method of claim 8, wherein the method further comprises screwing the fixator removed from within the receptacle into tissue of the patient.

10. The method of claim 1, wherein the delivery shaft comprises a temporary fixator coupled to the distal end thereof, and further wherein the method comprises temporarily fixating the delivery shaft to the anatomic target site using the fixator thereof prior to moving the elongated lead advancement member along the delivery shaft toward the anatomic target site.

11. The method of claim 1, wherein slidably coupling the connector of the elongated lead advancement member to the delivery shaft comprises sliding at least one ring over the elongated delivery shaft, the ring being positioned at the distal second end portion of the elongated lead advancement member.

12. A lead delivery device comprising:
   an elongated delivery shaft comprising a distal end insertable to an anatomic target site of a patient, wherein the elongated delivery shaft defines a delivery lumen;
   an elongated lead advancement member extending between a proximal first end portion and a distal second end portion, wherein the elongated lead advancement member is received in the delivery lumen, and wherein the elongated lead advancement member comprises:
      a movement member extending along a longitudinal axis, the movement member configured to be moved along the elongated delivery shaft; and
      a connector movably coupled to the elongated delivery shaft and movable along the elongated delivery shaft towards a location proximal to the distal end thereof as the movement member is pushed along the elongated delivery shaft; and
   a receptacle comprising an open end configured to receive a distal end of a lead and configured to removably attach the distal end of the lead within the receptacle, wherein the receptacle is coupled to the elongated lead advancement member such that the receptacle is movable along the elongated delivery shaft as the movement member is moved along the elongated delivery shaft.

13. The lead delivery device of claim 12, wherein the receptacle comprises an elastic enclosure configured to receive the distal end of the lead and removably attach the distal end of the lead within the receptacle.

14. The lead delivery device of claim 13, wherein the elastic enclosure is configured such that when the movement member is moved along and toward the distal end of the elongated delivery shaft, the distal end of the lead removably coupled within the receptacle is moved along the elongated delivery shaft with the movement member unless the lead is being held stationary by a user.

15. The lead delivery device of claim 13, wherein the elastic enclosure is configured such that, when the movement member is moved along and toward the distal end of the elongated delivery shaft, the distal end of the lead removably coupled within the receptacle is removed from the elastic enclosure when the lead is being held stationary by a user.

16. The lead delivery device of claim 12 wherein the receptacle comprises an elastic cap configured to receive the distal end of the lead and removably attach the distal end of the lead within the receptacle.

17. The lead delivery device of claim 12, wherein the receptacle comprises an enclosure configured to receive the distal end of the lead and into which a fixator at the distal end of the lead is removably screwed.

18. The lead delivery device of claim 17, wherein the receptacle is configured such that when the movement member is moved along and toward the distal end of the elongated delivery shaft, the distal end of the lead removably screwed within the receptacle is moved along the elongated delivery shaft with the movement member.

19. The lead delivery device of claim 12, wherein the delivery shaft comprises a temporary fixator coupled to the distal end thereof and deployable to temporarily fixate the elongated delivery shaft at the anatomic site, wherein the connector is movably coupled to the elongated delivery shaft and movable along the elongated delivery shaft towards a location proximal to the fixator as the movement member is pushed along the elongated delivery shaft.

* * * * *